Figure 1:
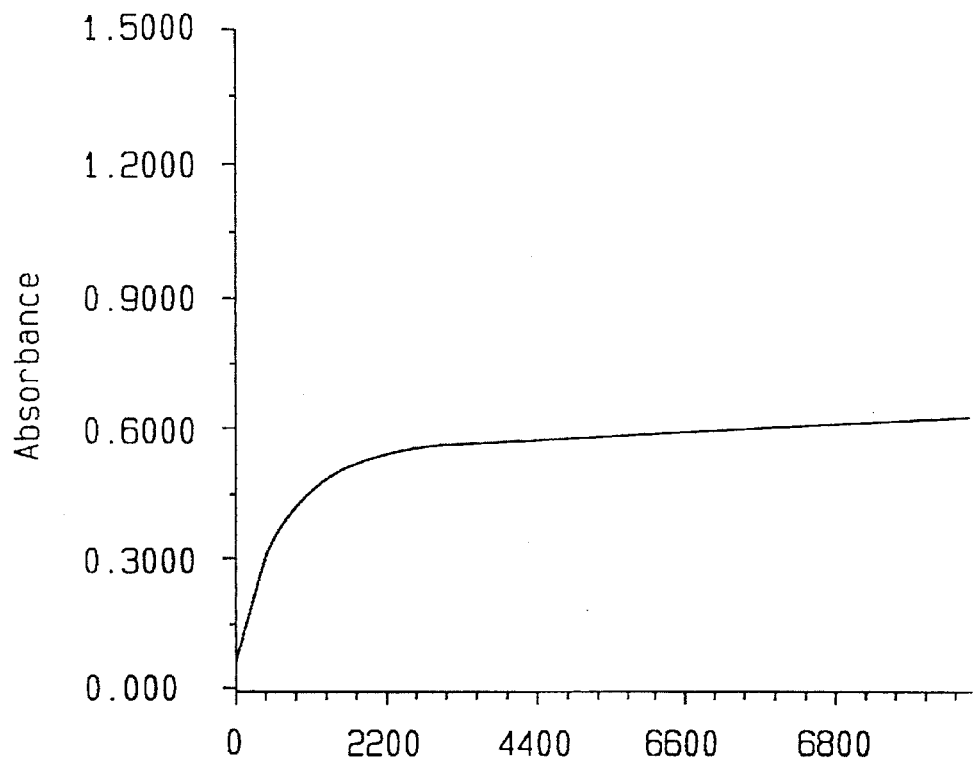

United States Patent [19]
Lebl et al.

[11] Patent Number: 5,635,598
[45] Date of Patent: Jun. 3, 1997

[54] SELECTIVELY CLEAVABE LINNERS BASED ON IMINODIACETIC ACID ESTERS FOR SOLID PHASE PEPTIDE SYNTHESIS

[75] Inventors: Michal Lebl; Viktor Krchnak; Petr Kocis, all of Oro Valley; Kit S. Lam, Tucson, all of Ariz.

[73] Assignee: Selectide Corporation, Tucson, Ariz.

[21] Appl. No.: 263,289

[22] Filed: Jun. 21, 1994

Related U.S. Application Data

[63] Continuation-in-part of Ser. No. 081,997, Jun. 23, 1993, abandoned, which is a continuation-in-part of Ser. No. 80,388, Jun. 21, 1993, abandoned.

[51] Int. Cl.$^6$ .................................................. A61K 38/02
[52] U.S. Cl. ........................ 530/334; 530/343; 530/345
[58] Field of Search ................................. 530/334, 343, 530/345

[56] References Cited

U.S. PATENT DOCUMENTS

| | | | |
|---|---|---|---|
| 3,963,701 | 6/1976 | Grisar et al. | 260/239 B |
| 5,066,716 | 11/1991 | Robey | 525/54.1 |
| 5,539,084 | 7/1996 | Geysen | 530/334 |

FOREIGN PATENT DOCUMENTS

| | | |
|---|---|---|
| 0 239 461 | 9/1987 | European Pat. Off. . |
| 0 274 998 | 7/1988 | European Pat. Off. . |
| 0 274 999 | 7/1988 | European Pat. Off. . |
| 0 322 348 | 6/1989 | European Pat. Off. . |
| 0 331 073 | 9/1989 | European Pat. Off. . |
| WO92/09395 | 8/1990 | WIPO . |
| WO92/00091 | 1/1992 | WIPO . |
| WO92/18144 | 10/1992 | WIPO . |

OTHER PUBLICATIONS

G. B. Fields and R. L. Noble, 1990, "Solid Phase Peptide Synthesis Utilizing 9–Fluorenylmethoxycarbonyl Amino Acids", Int. J. Peptide Protein Res. 35:161–214.

Atherton, 1981, "Peptide synthesis. Part 2. Procedures for solid–phase synthesis using N$^\alpha$–fluorenylmethoxycarbonylamino–acids on polyamide supports. Synthesis of substance P and of acyl carrier protein 65–74 decapeptide", J Chem Soc Perkin I:538–546.

Baleaux et al., 1986, "Glycoamidic ester group labile linkage in solid phase peptide synthesis: use with FMOC–protected amino acids", Int J Pept Protein Res 28:22–28.

Barany and Albericio, 1985, "A three–dimensional orthogonal protection scheme for solid–phase peptide synthesis under mild conditions", J Am Chem Soc 107:4936–4942.

Bray et al., 1991, "Direct cleavage of peptides from a solid support into aqueous buffer application in simultaneous multiple peptide synthesis", J Org Chem 56:6659–6671.

Hammer et al., 1990, "Practical approach to solid–phase synthesis of C–terminal peptide amides under mild conditions based on a photolysable anchoring linkage", Int J Pept Protein Res 36:31–45.

Kneib–Cordonier et al., 1990, "Orthogonal solid–phase synthesis of human gastrin–I under mild conditions", *Peptides—Chemistry, Structure and Biology*, Rivier and Marshall, eds., pp. 895–897.

Lam et al., 1991, "A new type of synthetic peptide library for identifying ligand–binding activity", Nature 354:82–84.

Landon, 1977, "Cleavage at Aspartyl–Prolyl Bonds", Methods in Enzymology 47:145–149.

Lebl et al., 1993, "Multiple release of equimolar amounts of peptides from a polymeric carrier using orthogonal linkage–cleavage chemistry", Int J Peptide Protein Res 41:201–203.

Maeji et al., 1990, "Multi–pin peptide synthesis strategy for T cell determinant analysis", J Immunol Methods 134:23–33.

Stewart and Young, 1984, "The Polymer Support", in *Solid Phase Peptide Synthesis*, Second Edition, pp. 8–9.

Van der Zee et al., 1989, "Efficient mapping and characterization of a T cell epitope by the simultaneous synthesis of multiple peptides", Eur J Immunol 19:43–47.

Wang, 1976, "Solid phase synthesis of protected peptides via photolytic cleavage of the α–methylphenacyl ester anchoring linkage", J Org Chem 41:32–58.

Marshall et al., J. Org. Chem., 35:867 (1970).

Kenner et al., Chem. Commun. 636 (1971).

"The Peptide Analysis, Synthesis, Biology", E. Gross, J. Meienhofer Eds., Academic Press, New York, v.3, p. 209.

Chemical Abstracts 110:135705 (1989).

Chemical Abstracts 115:183681S.

Orlowski et al., J. Org. Chem. 41(23):3701–3705 (1976).

Funakoshi et al., Chem. Commun. 5:382–384 (1988).

Pátek and Lebl, Tetr. Lett. 32:3891–3894 (1991).

Pátek and Lebl, Tetr. Lett. 31:5209–5212 (1990).

Albercio et al., Int J. Pept. Prot. Res. 30:206–216 (1987).

Caprino et al., Accounts of Chemical Research, 20:(11):401–407 (1987).

Hermanson, "Immobilized Affinity Ligand Techniques" pp. 98–99 and 180–182, 1992.

*Primary Examiner*—David Lukton
*Attorney, Agent, or Firm*—Pennie & Edmonds

[57] ABSTRACT

The present invention is directed to linkers based on ester bond linkages, especially iminodiacetic acid ester bond linkages, for use in solid phase peptide synthesis. In particular, the invention is directed to cleavable linkers that can release peptide from the solid phase support under relatively mild conditions by formation of a diketopiperazine or other cyclic structure, such that the cyclic structure remains on the solid phase support, and, in a second cleavage, under more stringent conditions of high pH. The invention is further directed to solid phase supports prepared with multiple cleavable linkers, including a linker that is cleaved by formation of a cyclic product. One such second linker is an ester of hydroxymethylbenzoic acid, or esters formed by carboxy groups of aspartic or glutamic acid.

47 Claims, 8 Drawing Sheets

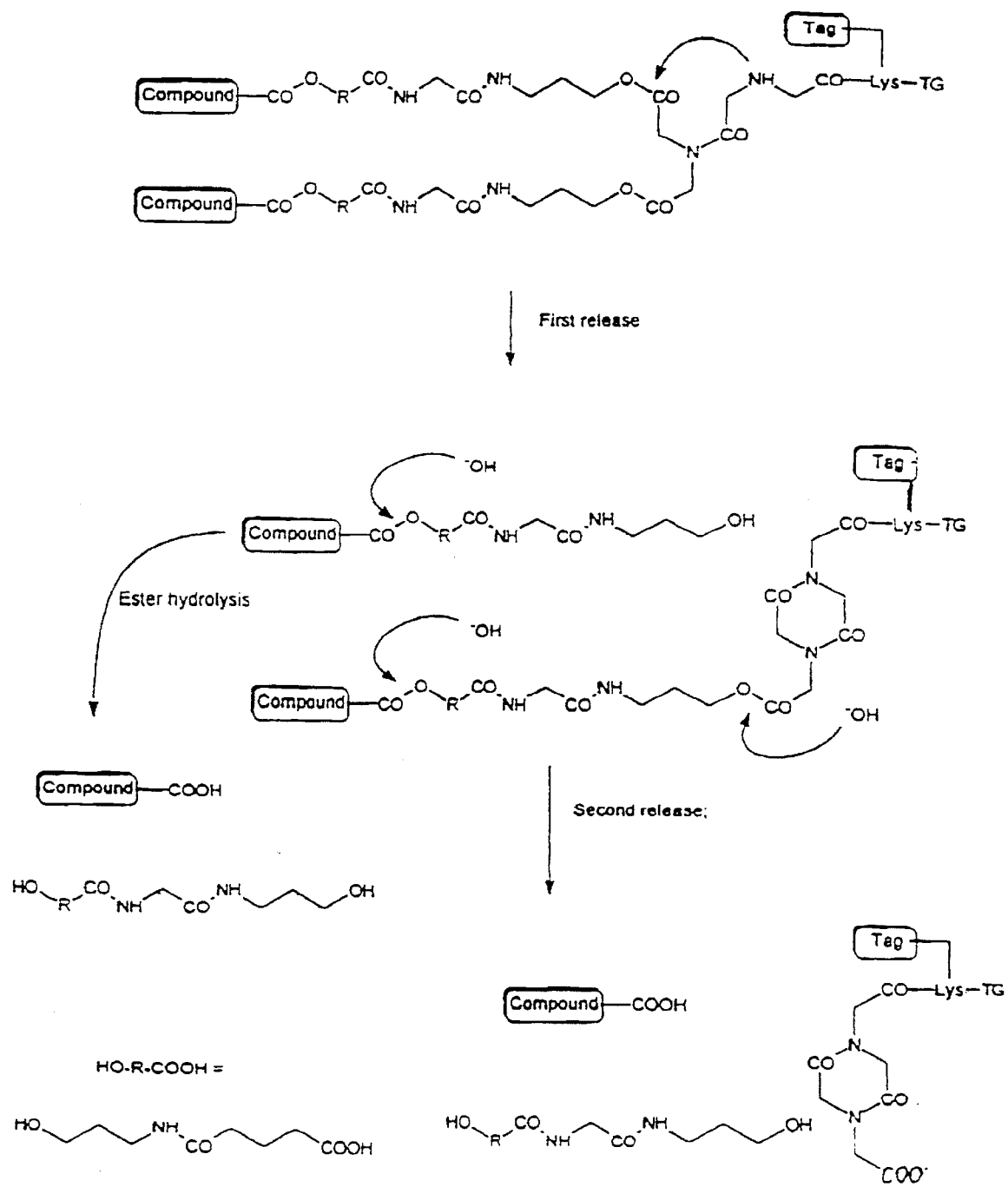

SELECTIVELY CLEAVABE LINNERS BASED ON IMINODIACETIC ACID ESTERS FOR SOLID PHASE PEPTIDE SYNTHESIS

The present application is a continuation-in-part of application Ser. No. 08/081,997 now abandoned, filed Jun. 23, 1993, which was a continuation-in-part of application Ser. No. 08/080,388 now abandoned, filed Jun. 21, 1993, both of which are incorporated herein by reference in their entirety.

TABLE OF CONTENTS

1. FIELD OF THE INVENTION
2. BACKGROUND OF THE INVENTION
3. SUMMARY OF THE INVENTION
  3.1 ABBREVIATIONS
4. BRIEF DESCRIPTION OF THE DRAWINGS
5. DETAILED DESCRIPTION OF THE INVENTION
  5.1. LINKERS
    5.1.1. ESTER LINKERS CLEAVABLE AT MODERATE pH
    5.1.2. ESTER LINKERS CLEAVABLE AT HIGHER pH
    5.1.3. RELEASE OF COMPOUNDS WITH FREE CARBOXY GROUP
  5.2. MULTIPLE CLEAVABLE LINKERS
    5.2.1. DOUBLE CLEAVABLE LINKER UTILIZING ESTER BOND AND METHIONINE BOND CLEAVAGE
  5.3. USE OF THE LINKER FOR PEPTIDE SYNTHESIS
  5.4. BIOACTIVITY ASSAYS WITH THE RELEASABLE LINKERS
    5.4.1. RANDOM PEPTIDE LIBRARIES
  5.5. PHARMACEUTICAL USES OF THE CLEAVABLE LINKERS
6. EXAMPLE: IMINODIACETIC ACID BASED LINKERS FOR TWO STAGE RELEASE OF PEPTIDES FROM SOLID SUPPORT
  6.1. MATERIALS AND METHODS
    6.1.1. PREPARATION OF IDA LINKERS
    6.1.2. GENERAL PROTOCOL FOR SOLID PHASE SYNTHESIS
    6.1.3. SYNTHESIS OF DOUBLY CLEAVABLE LEU ENKEPHALIN
    6.1.4. Trp-Gly-PAOH CONTROL RELEASE
    6.1.5. PEPTIDE RELEASE KINETICS
  6.2. RESULTS
  6.3. DISCUSSION: LINKERS BASED ON AN IDA-IDA MOTIF
7. EXAMPLE: METHIONINE CONTAINING LINKERS
8. EXAMPLE: ADDITIONAL CLEAVABLE LINKERS WITH ESTERS

1. FIELD OF THE INVENTION

The present invention is directed to linkers based on ester bond linkages, especially iminodiacetic acid ester bond linkages, for use in solid phase peptide synthesis. In particular, the invention is directed to cleavable linkers that can release peptide from the solid phase support under relatively mild conditions by formation of a diketopiperazine or other cyclic structure, such that the cyclic structure remains on the solid phase support, and, in a second cleavage, under more stringent conditions of high pH. The invention is further directed to solid phase supports prepared with multiple cleavable linkers, including a linker that is cleaved by formation of a cyclic product. One such second linker is an ester of hydroxymethylbenzoic acid, or esters formed by carboxy groups of aspartic or glutamic acid.

2. BACKGROUND OF THE INVENTION

Many solid phase resins and handles for peptide synthesis are available in the art, as is described in Fields and Noble, 1990, Int. J. Pept. Protein Res. 35:161–214. To be useful, handles must be stable to the reaction conditions of peptide synthesis, but when the synthesis is complete, the handle needs to allow for cleavage of the peptide from the solid support.

Less common, but no less useful, are selectively cleavable linkers. These linkers can act as handles; alternatively, the linker can be coupled to another handle. The useful feature of certain of these linkers is that they can be cleaved under much milder conditions than are associated with handles, e.g., under mildly basic or acidic conditions, rather than highly acidic conditions associated with peptide cleavage, e.g., in hydrogen fluoride (HF) or trifluoroacetic acid (TFA).

Ultraviolet light sensitive linkers, such as ONb (see Barany and Albericio, 1985, J. Am. Chem. Soc. 107:4936–4942) have been used. Other cleavable linkers require hydrogenolysis or photolysis. Examples of other photosensitive (photocleavable) linkers are found in Wang (1976, J. Org. Chem. 41:32–58), Hammer et al. (1990, Int. J. Pept. Protein Res. 36:31–45), and Kreib-Cordonier et al. (1990, in Peptides-Chemistry, Structure and Biology, Rivier and Marshall, eds., pp. 895–897).

Landen (1977, Methods Enzym. 47:145–149) used aqueous formic acid to cleave Asp-Pro bonds; this approach has been used to characterize T-cell determinants in conjunction with the Geysen pin synthesis method (Van der Zee et al., 1989, Eur. J. Immunol. 191:43–47). However, treatment of peptides with formic acid is undesirable, especially if the treated peptides are to be used in a biological assay.

Other potential linker groups cleavable under basic conditions include those based on p-(hydroxymethyl)benzoic acid (Atherton et al., 1981, J. Chem. Soc. Perkin I:538–546) and hydroxyacetic acid (Baleaux et al., 1986, Int. J. Pept. Protein Res. 28:22–28). Geysen et al. (1990, J. Immunol. Methods 134:23–33) reported peptide cleavage by nucleophilic attack on a carboxy-terminal ester of proline, giving rise to a two-ring derivative of diketopiperazine. However, the "diketopiperazine" method described by Geysen produces peptides which carry a C-terminal diketopiperazine moiety (Bray et al., 1991, J. Org. Chem. 56:6659–6671). This is a disadvantage, because the heterocyclic moiety can affect binding activity or biological activity of the released peptide. International Patent Publication WO 90/09395 (Geysen, published Aug. 23, 1990) suggests orienting a dipeptide cleavable linker so that the heterocycle remains on the solid support.

Moreover, recently techniques have been developed that make possible the preparation of libraries of $10^6$ to $10^7$ or more peptides attached to solid phase supports, in which each particle of solid phase support contains a single peptide species (International Patent Publication No. WO92/00091, published Jan. 9, 1992). These libraries are used advantageously when the peptide species can be sequentially cleaved in substantially equimolar amount from the solid phase support, so that each peptide species can be tested in more than one assay for its activity, or peptides can be tested in mixtures, followed by separation of all the resin particles from a positive mixture for further testing. These libraries also provide for an equimolar amount of each peptide to remain on the solid phase support for sequencing those peptides that, when released from the solid support, exhibit the activity of interest.

Thus there is a need in the art for a releasable linker that yields a peptide of substantially unaltered structure, and in particular, which does not have a diketopiperazine moiety attached. Moreover, there is a need for release of peptides to a solution compatible with biological tests.

Furthermore, there is a need in the art for multiply cleavable linkers, in which cleavage of each linker is independent of cleavage of the others, i.e., orthogonal to cleavage of the others, thus providing for sequential cleavage of the same or different peptide species from a solid support in equimolar ratios.

Citation of any reference in this application is not to be deemed an admission that such reference is available as "prior art."

3. SUMMARY OF THE INVENTION

The present invention is directed to linkers based on an ester bond linkages, in particular iminodiacetic acid linkers, for solid phase peptide synthesis. Such linkers provide for cleavage of the peptide from the solid phase support. In one aspect of the invention, the ester bond is cleaved with formation of a diketopiperazine or other cyclic structure that remains on the solid support. The peptide released by cleavage of the ester bond can include a C-terminal carboxyhydroxyalkylamide group. In a further embodiment, the ester bond is cleaved under relatively strong basic conditions. Preferably, a tandem arrangement of iminodiacetic acid groups provides for both types of ester bonds.

In a preferred aspect of the invention, the linker is iminodiacetic acid (IDA). The carboxylic acid moieties of IDA, which can form an ester bond with a peptide, can provide for multiple cleavage. The first cleavage reaction can occur by an internal nucleophile attack with diketopiperazine formation. This reaction occurs at pH greater than about 6.0, preferably greater than 7.0, by attack of a free amine of an amino acid coupled to the imino group of IDA. The free amine attacks one of the esters. Alternatively, the imino group on an amino acid-ester coupled to one of the carboxylic acids can act as a nucleophile towards the ester. More preferably, the imino group of an IDA attacks an ester formed with the carboxylic acid of a second IDA, which second IDA is couple via an amide linkage with the imino group of the second IDA to a carboxylic acid of the first IDA.

The second cleavage reaction can occur by an external nucleophile attack, e.g., hydrolysis under relatively strong basic conditions.

The invention is further directed to solid phase supports comprising more than one cleavable linker, in which at least one such linker can be cleaved with formation of a cyclic structure, e.g., a diketopiperazine, attached to the solid phase support. The linkers can further comprise a linker such that upon cleavage, the diketopiperazine is attached to the released peptide. In a further embodiment, the ester bond linkage can be to a reactive carboxylic acid, such as hydroxymethylbenzoic acid. Other cleavable linkers that can be attached to the solid phase support in the multiple cleavable linker embodiment of the invention include but are not limited to photocleavable linkers and acid cleavable linkers. The solid phase support can further comprise a traditional handle.

The invention is further directed to methods of cleaving multiple linkers sequentially, so that at each cleavage step only one linker is cleaved, and a fraction of the peptide is released.

The cleavable linker of the invention can be used for biological or binding assays of peptides or other test compounds. Alternatively, the linked compound can be a coding molecule as is disclosed in the U.S. patent application Ser. No. 068,327, filed May 27, 1993 which is incorporated by reference herein. The iminodiacetic acid linkers are particularly advantageous for these type of assays since the released peptide lacks a diketopiperazine moiety.

Use of iminodiacetic acid (IDA) as a linker has great advantages over dipeptide linkers that form diketopiperazines. IDA is a much less expensive reagent. Furthermore, as shown in a specific example, infra, IDA-IDA linkers undergo rapid cyclization with release of peptide, even at pH less than 7. In a specific example, the release occurs at about pH 6.5.

Another advantage of the present invention is that the rate of release of a dipeptide diketopiperazine linker can be controlled by selection of appropriate amino acid combinations, thus providing for rapid or, alternatively, slow release, depending on the biological assay of interest. Yet a further advantage of the present invention is that the peptides can be released to a solution compatible with biological tests.

In another aspect, the invention provides for in vivo release of a pharmaceutical agent, such as a peptide. A particular advantage of the cleavable linkers of the invention is that the rate of cleavage can be controlled, depending on the desired rate of release of the pharmaceutical agent, and the released pharmaceutical agent will not have a diketopiperazine moiety attached to it. Such releasable pharmaceutical agents are preferred for oral administration, in which an inert solid support, to which the diketopiperazine or other cyclic moiety is attached after cleavage, can be excreted.

Yet another advantage of the present invention is that multiple cleavable linkers that can be cleaved sequentially, i.e., orthogonally, are provided.

3.1 ABBREVIATIONS

Abbreviations used follow the recommendations of the IUPAC-IUB Commission on Biochemical Nomenclature (Eur. J. Biochem. 1984, 138:9). Amino acid symbols denote the L-configuration where applicable. Other abbreviations are as follows:

| | |
|---|---|
| AA | amino acid |
| AcOH | acetic acid |
| Alloc | allyloxycarbonyl |
| Boc | butyloxycarbonyl |
| Bu$^t$ | tert-butyl |
| Bzl | benzyl |
| Ddz | 2-(3,5-dimethoxyphenyl)propyloxycarbonyl |
| DIC | N,N'-diisopropylcarbodiimide |
| DIEA | N,N'-diisopropylethylamine |
| DCM | dichloromethane |
| DKP | diketopiperazine |
| DMAP | 4-dimethylaminopyridine |
| DMF | N,N-dimethylformamide |
| EDT | 1,2-ethanedithiol |
| HOBt | 1-hydroxybenzotriazole |
| IDA | iminodiacetic acid |
| Npys | 2-nitropyridylsulfenyl |
| PA, PAO | propanyl amine (or amide) ester |
| PAOH | propanol amine (or amide) |
| RP-HPLC | reversed-phase high performance liquid chromatography |
| SPPS | solid-phase peptide synthesis |
| TFA | trifluoroacetic acid |
| TG | TentaGel (resin) |
| Z | benzyloxycarbonyl |

4. BRIEF DESCRIPTION OF THE DRAWINGS

FIG. 1. Reaction kinetics of the release of the peptide Trp-Gly-propanolamide (PAOH) from an IDA linker at pH 8.3. Absorbance at 280 nm (tryptophan) versus time. The linker was IDA-Pro-OPA<-Gly<-Trp<-Fmoc (compound 7).

Figure 2A:
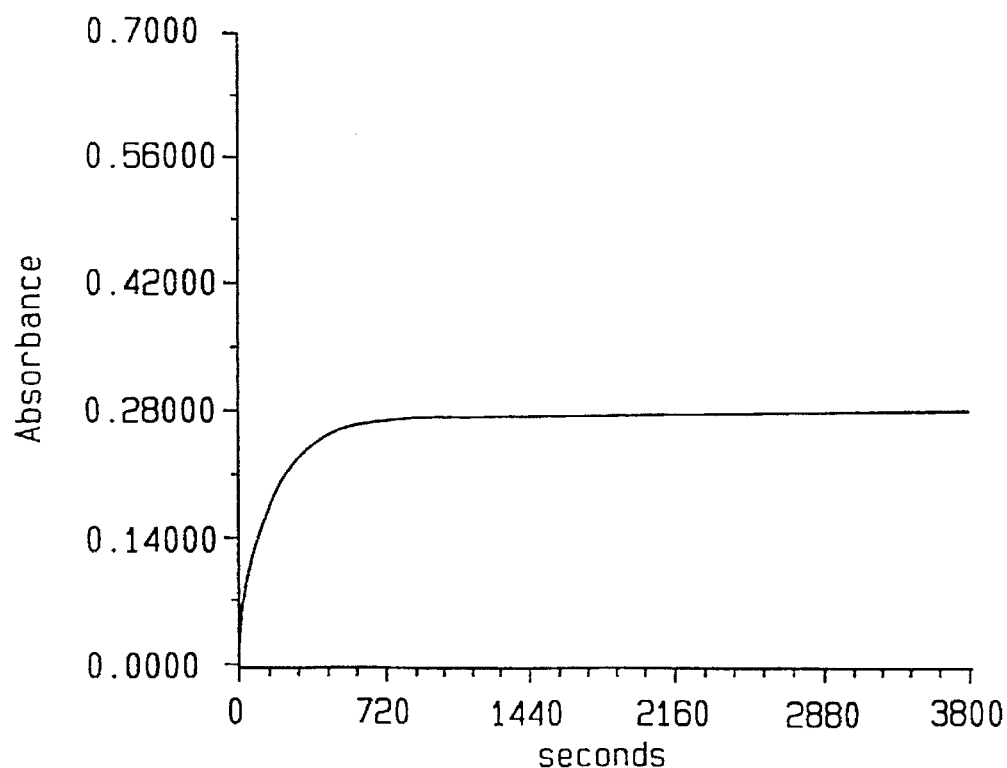
Figure 2B:
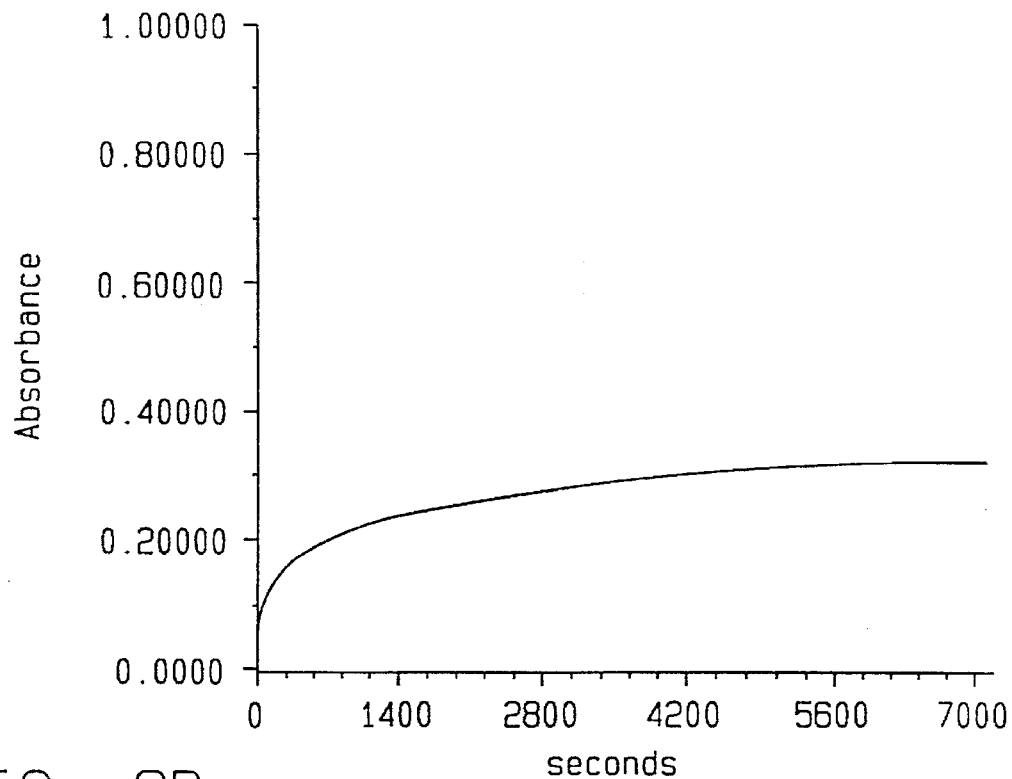

FIGS. 2A–2B. Reaction kinetics of the release of the peptide Trp-Gly-PAOH from linker-resin construct I. The first release occurred at pH 8.3 (A) and subsequently, the second release occurred at pH 13.2 (B).

Figure 3:
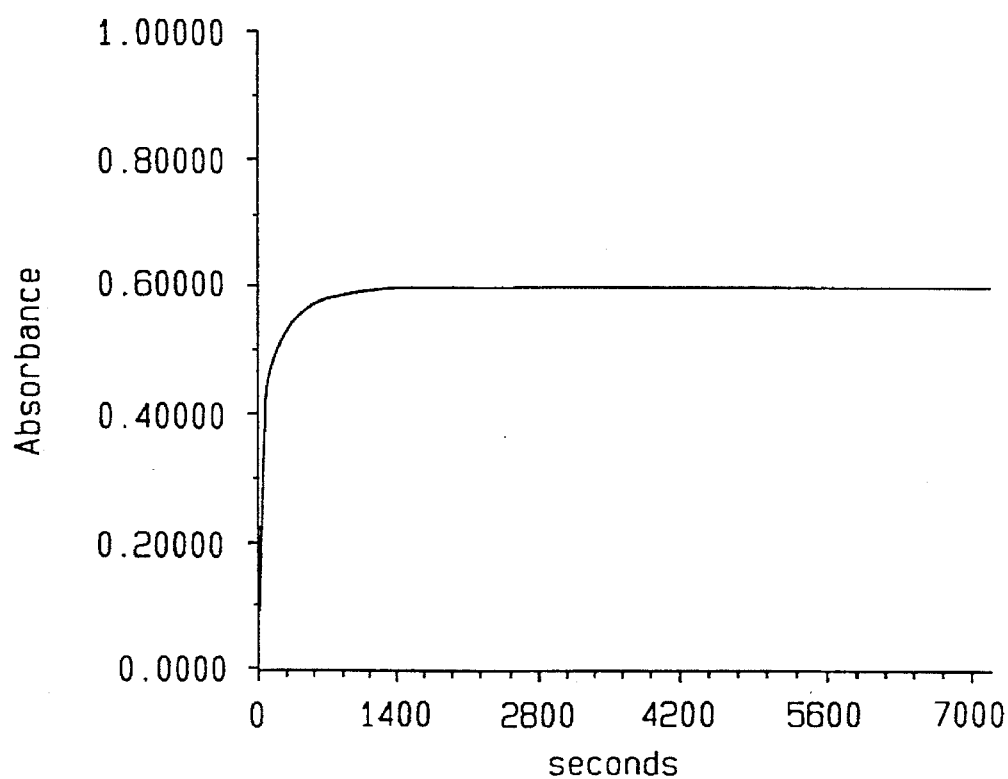

FIG. 3. Reaction kinetics of the release of the peptide Trp-Gly-PAOH from linker construct II at pH 8.3. Release occurs by attack of the α-amino group of Gly, coupled via an amide bond to the imino group of the first IDA, on the peptide ester formed with one of the arms of IDA.

FIGS. 4A–4D. Reaction kinetics of the release of the peptide Trp-Gly-PAOH from a double cleavable linker using an IDA-IDA strategy. The release kinetics were determined at pH 4.0 (A), 6.5 (B) and 8.5 (C). Release kinetics for a first (pH 8.5) and second (pH 13.2) release were also observed (D).

Figure 5A:
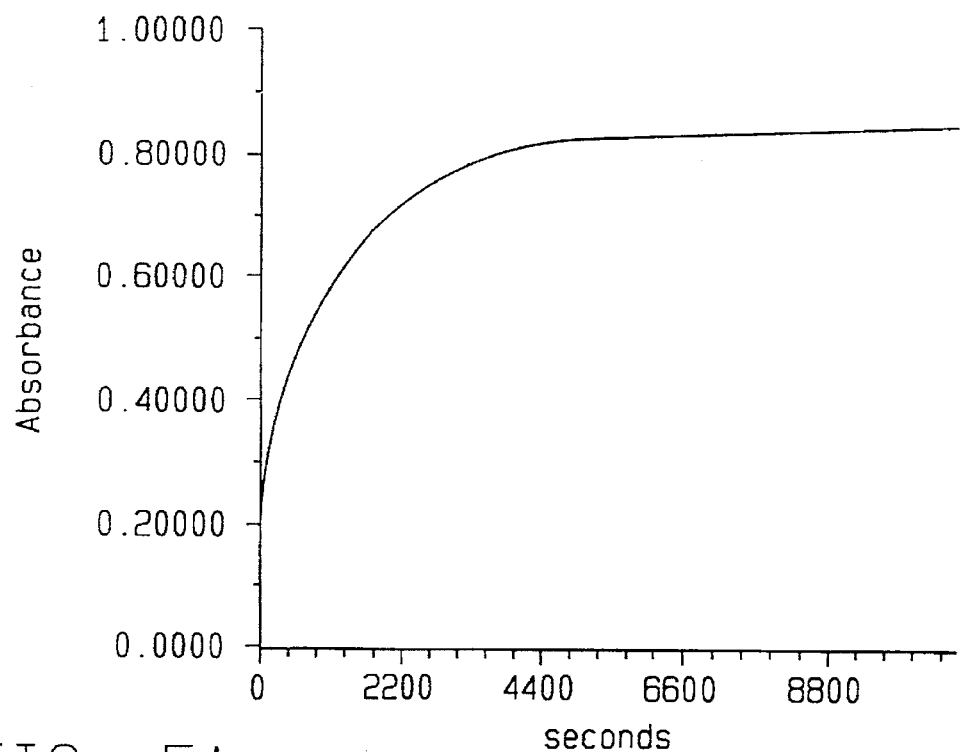
Figure 5B:
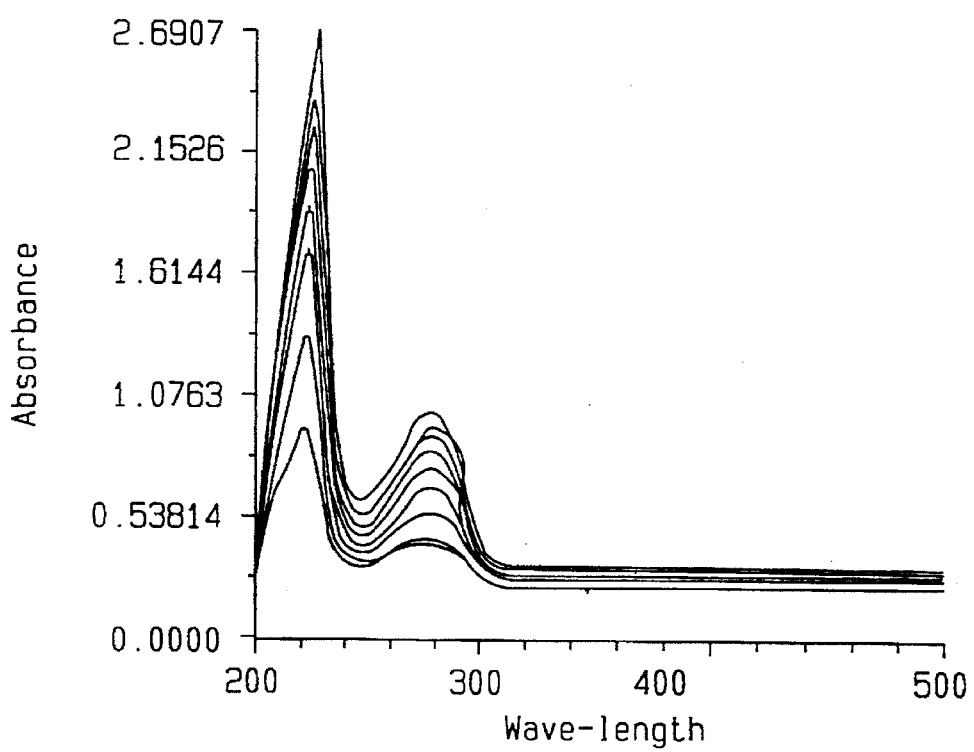

FIGS. 5A–5B. Release of the peptide Trp-Gly-Gly-propanolamide. The peptide was coupled to the solid phase support using a diketopiperazine linker. The absorbance in solution (tryptophan and amide bonds) was monitored as a function of time. A. Absorbance vs. time profile of the released peptide, showing nearly quantitative release of peptide within 2 hours. B. Time resolved absorbance spectra of the released peptide. Note that the spectra are identical, indicating that the increased absorbance over time resulted from released peptide, rather than an artifact.

Figure 6:
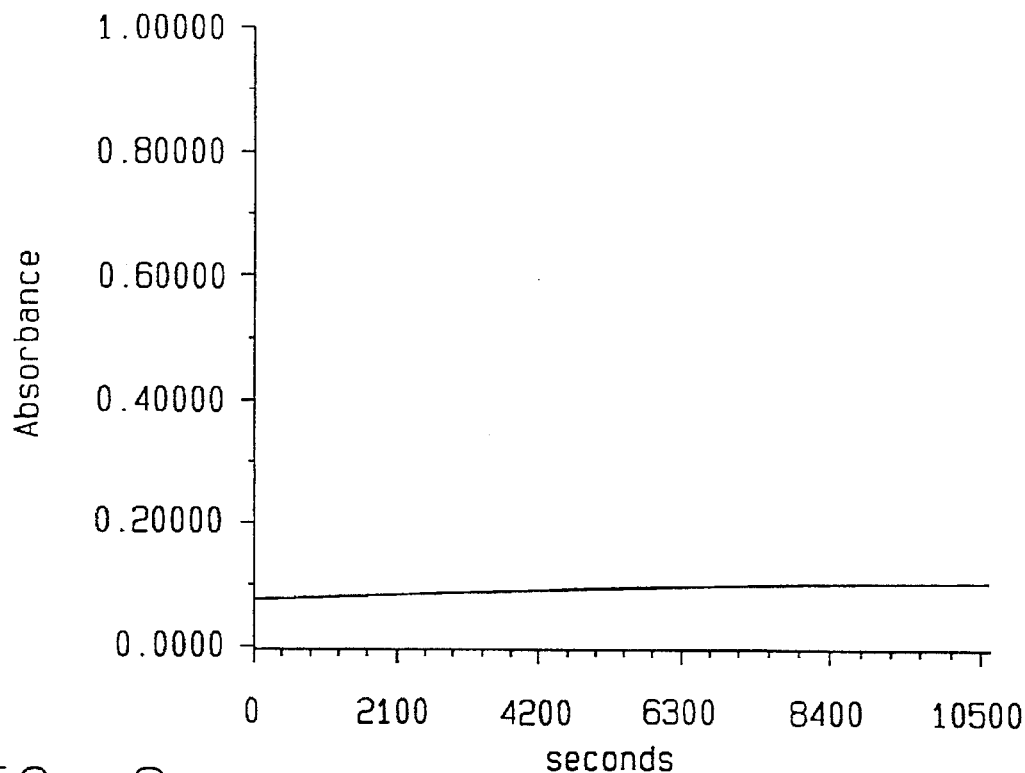

FIG. 6. Stability test of a glutamate linker at pH 8.46. The absorbance vs. time plot shows substantially no release of peptide for 7.5 hours.

Figure 7A:
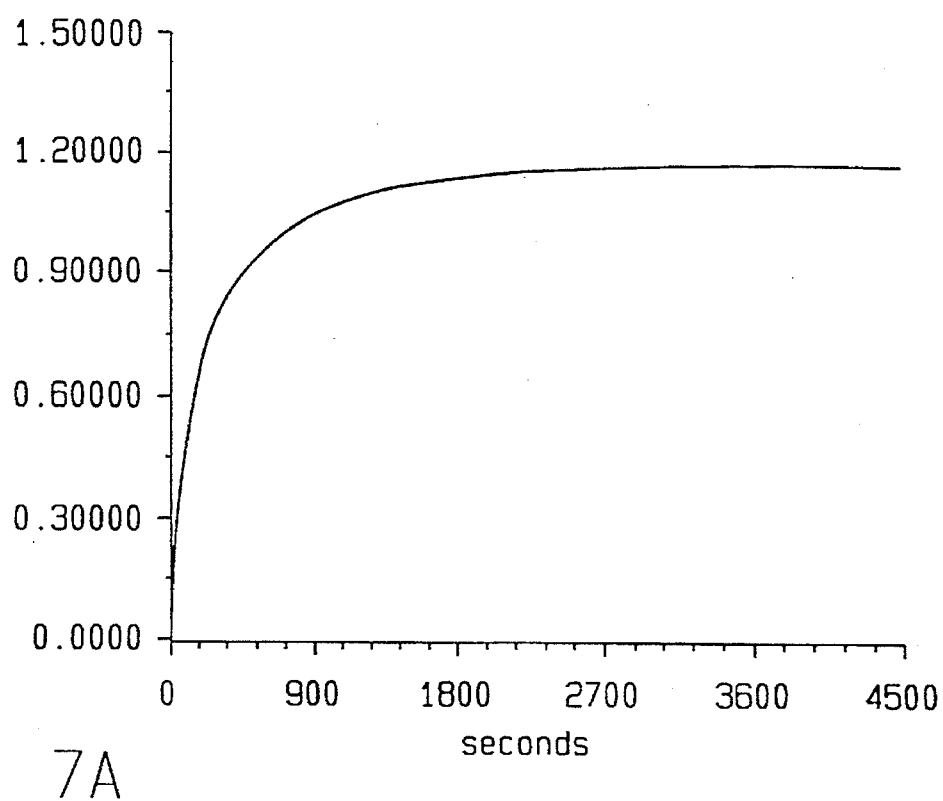
Figure 7B:
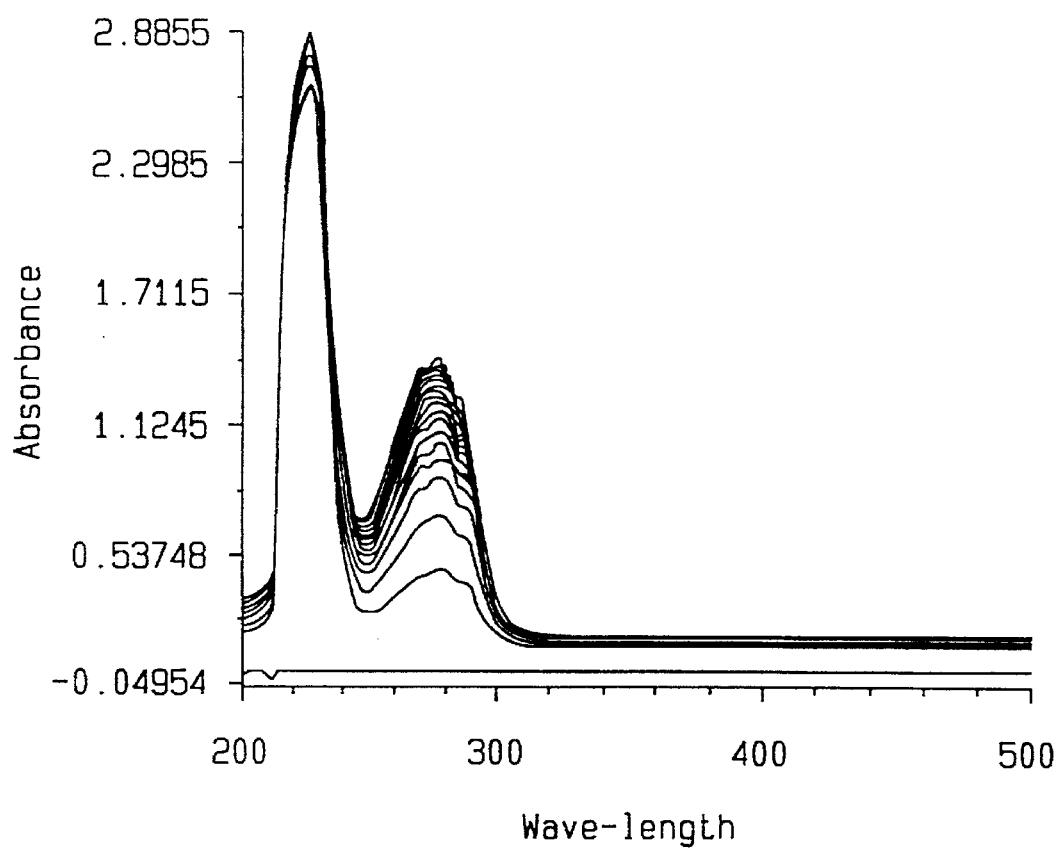

FIGS. 7A–7B. Release of peptide coupled to the solid phase support via a glutamate linker. This peptide-linker combination had already been treated with solution at pH 8.5, which did not result in release of the peptide. The peptide-linker conjugate was treated with NaOH, pH 13.2 and the release of Gly-Trp-Gly propanolamide was monitored spectrophotometrically. A. Absorbance vs. time plot, showing increasing absorbance and nearly quantitative release within one hour. B. Time resolved absorbance spectra of the released peptide. Note that the spectra are identical, indicating that the increased absorbance over time resulted from released peptide, rather than an artifact.

FIG. 8. Two stage release of peptides from linkers having two ester bonds so that the peptide is released having a free carboxy moiety.

5. DETAILED DESCRIPTION OF THE INVENTION

The present invention is directed to linkers based on an ester bond linkages for solid phase peptide synthesis, in particular, iminodiacetic acid linkers. Such linkers provide for cleavage of the peptide from the solid phase support. In one aspect of the invention, the ester bond is cleaved with nucleophilic attack of an internal nucleophile that forms a cyclic compound, e.g., a diketopiperazine (DKP), that remains on the solid support. The peptide released by cleavage of the ester bond can include a C-terminal hydroxyalkylamide group, e.g., methanolamide, ethanolamide, or propanolamide. In a further embodiment, the ester bond is cleaved by an external nucleophile (basic conditions). In a preferred aspect, when the linker is IDA-IDA, two ester bond cleavable linkages are provided, one cleavable via DKP formation and the second via treatment under conditions of high pH.

The invention is further directed to solid phase supports comprising more than one cleavable linker, in which at least one such linker contains an ester bond linkage to the peptide. Preferably, such a linker is IDA, and more preferably, IDA-IDA. An additional linker can be cleaved with formation of a cyclic structure, e.g., a diketopiperazine, attached to the solid phase support, or with the diketopiperazine attached to the released peptide. The nucleophilic groups of linkers that cleave by formation of a cyclic product can be orthogonally protected. The orthogonal protecting groups can be removed sequentially, providing for sequential releases. In another embodiment, the ester bond linkage can be to a reactive carboxylic acid, such as hydroxymethylbenzoic acid. Other cleavable linkers that can be attached to the solid phase support in the multiple cleavable linker embodiment of the invention include but are not limited to photocleavable linkers and acid cleavable linkers. The solid phase support can further comprise a traditional handle.

The invention is further directed to methods of cleaving multiple linkers sequentially, so that at each cleavage step only one linker is cleaved, and an equimolar fraction of the peptide is released.

In a specific embodiment, infra, the release of peptide is based on cleavage of an ester bond with an internal nucleophile by rapid formation of a cyclic, e.g., diketopiperazine, structure under weakly basic conditions. Preferably the internal nucleophile is the imino functionality of an IDA linker, which can attack an ester bond formed by any α-carboxylic acid of a molecule coupled to one of the branching acetic acid groups of IDA. In one aspect, the carboxylic acid ester is an α-carboxyl of an amino acid; preferably, it is a carboxyl of an IDA. In another embodiment, the free α-amino group of any molecule coupled to the imino group of IDA can attack an ester formed with one of the carbonyl groups of the IDA. In one aspect, the α-amine can be part of an amino acid. In a specific embodiment, infra, the amino acid is glycine.

In a further embodiment, the release is effected by treatment with dilute sodium hydroxide or ammonia in methanol or by exposure to ammonia gas.

In yet a further embodiment, both linkages are used. In another embodiment both linkages are provided on a single linker. Preferably such a linker is IDA-IDA.

In yet another embodiment, different linkers with five levels of cleavability are used, including the ester linkage linkers.

As used herein, the term alkyl includes but is not limited to $C_1$ to about $C_{10}$ alkane, alkene and alkyne (i.e., saturated and unsaturated hydrocarbons). For example, an alkyl group may be methyl, ethyl, ethenyl, propyl, propenyl, propynyl, etc. The term alkyl as used herein includes branched chain as well as linear chain groups, and cyclic alkyl.

As used herein, the term "cleavable linker" is defined as a spacer molecule characterized by having a bond that can be cleaved under relatively mild conditions. The linker has one functional group that binds to a solid phase support, or to a handle on a solid phase support. The linker has a second functional group that can be conjugated to an amino acid or a peptide or any organic compound of interest that provides a suitable functional group for coupling to the linker. The linkers of the invention can have a third functional group, a nucleophilic group, that can attack the ester bond and cleave it thereby. The linker provides for cleavage of the peptide after synthesis is complete.

As used herein, the term "solid phase support" is not limited to a specific type of support. Rather a large number of supports are available and are known to one of ordinary skill in the art. Solid phase supports include silica gels, resins, derivatized plastic films, glass beads, cotton, plastic beads, alumina gels, polysaccharides. A suitable solid phase support may be selected on the basis of desired end use and suitability for various synthetic protocols. For example, for peptide synthesis, solid phase support may refer to resins such as p-methylbenzhydrylamine (pMBHA) resin (Peptides International, Louisville, Ky.), polystyrene (e.g., PAM-resin obtained from Bachem Inc., Peninsula Laboratories, etc.), poly (dimethylacrylamide)-grafted styrene co-divinyl-benzene (e.g., POLYHIPE® resin, obtained from Aminotech, Canada), polyamide resin (obtained from Peninsula Laboratories), polystyrene resin grafted with polyethylene glycol (TentaGel®, Rapp Polymere, Tubingen, Germany) polydimethylacrylamide resin (obtained from Milligen/Biosearch, California), or Sepharose (Pharmacia, Sweden).

In one embodiment, the solid phase support may be suitable for in vivo use, i.e., it may serve as a carrier for or support for direct applications of the peptide or other biologically active compound (e.g., TentaGel, Rapp Polymere, Tubingen, Germany). In a particular embodiment, the solid phase support may be palatable and orally consumable.

The term "peptide" is used herein in its broadest sense to refer to a compound of two or more subunit amino acids, amino acid analogs or peptidomimetics. The subunits may be linked by peptide bonds. As used herein the term "amino acid" refers to either natural and/or unnatural or synthetic amino acids, including glycine and both the D and L optical isomers, and amino acid analogs and peptidomimetic subunits. As used herein, a peptidomimetic is a molecule that exhibits properties similar to a peptide without having a peptide chemical structure. The peptides may comprise D-amino acids, a combination of D- and L-amino acids, and various "designer" amino acids (e.g., β-methyl amino acids, Cα-methyl amino acids, and Nα-methyl amino acids, etc.) to convey special properties to peptides. Additionally, by assigning specific amino acids at specific coupling steps, peptides with α-helices, β turns, β sheets, γ-turns, and cyclic peptides can be generated.

5.1. LINKERS

The selectively cleavable linkers based on an ester bond linkage are characterized by being sensitive to nucleophilic attack. Preferably, the linker is iminodiacetic acid.

The present invention further provides strategies for increasing or decreasing the sensitivity of a specific ester bond to nucleophilic attack. These strategies include but are not limited to affecting the nucleophilicity of the nucleophile; affecting the accessibility of the ester carbonyl; and affecting the tendency to cyclize, in the case where the nucleophile attacks the ester carbonyl in a cyclization reaction. By altering these parameters, the invention provides for control over the pH of the release reaction, control over the rate of release, and control over the quantity of peptide released.

For clarity of discussion, the invention is described in the subsections below by way of example for the (i) diketopiperazine-forming linkers (linkers containing an internal nucleophile and forming cyclic structures that remain attached to the solid phase support after cleavage) and (ii) hydroxymethylbenzoic, glutamic or aspartic acid linker (linker cleavable only by external nucleophilic attack). However, the principles may be analogously applied to other ester linkage-based linkers.

5.1.1. ESTER LINKERS CLEAVABLE AT MODERATE pH

In one embodiment, the linkers of the invention release a peptide alcohol upon formation of a diketopiperazine, which remains on the solid phase support. Such linkers are termed herein "diketopiperazine (DKP) linkers." The present invention is based in part on the observation that peptide coupled to an aliphatic alcohol amine, in which the amine group forms an amide bond with the C-terminal carboxyl of the peptide and the alcohol group is attached via an ester bond to a cyclizeable linker, can be cleaved from the linker under mild conditions. Upon deprotection of the nucleophile on the linker, free nucleophile can attack the ester bond, forming a cyclic product attached to the solid support, e.g., the diketopiperazine, and releasing the peptide.

The recognition of iminodiacetic acid as an alpha-amino acid involved in diketopiperazine formation allows the design of novel double cleavable linkers. Iminodiacetic acid is a suitable key compound for design of double cleavage linkers for several reasons: (i) The imino group is in an α-position relative to carboxyl groups; (ii) both carboxyl groups are chemically equal (identical); (iii) as a N-substituted amino acid it is prone to cyclization via DKP formation with practically any other α-amino acid; (iv) it is not chiral; (v) its price is more than competitive. In general, there are three variations to construct IDA based linker. They can be schematically depicted as dipeptides containing Aaa-IDA, IDA-Aaa, or IDA-IDA, where Aaa is any alpha-amino acid, preferably such that is prone to cyclization via DKP formation. The position of IDA in such a dipeptide seems not to be important. This is not true for other combinations of amino acids, such as Glu-Pro and Pra-Glu, as described infra.

Thus, in a specific embodiment, infra, the linker is IDA, in which one carboxyl is used to couple to the solid phase support, and the other carboxyl is coupled to an alcohol derivative of a peptide, and an amine of an amino acid coupled to the imino group can act as a nucleophile. In another embodiment, infra, the linker is IDA coupled to a solid support on one carboxyl and to an amino acid on the other carboxyl. The α-carbonyl of the imino acid is used to form an ester, and the imino group of the IDA can attack the ester. In a more preferred embodiment, branching IDA linkers provide (1) a free imino group that can participate in nucleophilic attack of an ester to form DKP; and (2) at least one ester bond cleavable by a cyclization reaction and one ester bond cleavable by hydrolysis.

In another embodiment, infra, the linker is a dipeptide of the sequence glutamic acid-proline. In another embodiment, infra, the linker is a dipeptide of the sequence proline-glutamic acid. In yet another embodiment, the linker is a dipeptide of the sequence lysine-proline. The N-terminal amino group of the dipeptide acts as the nucleophile in the cleavage reaction. Generally, any species of dipeptide can be used with the proviso that the dipeptide contain a side chain functional group for coupling to the solid phase support. In specific embodiments, infra, the γ-glutamyl group of glutamic acid is used to couple with the solid phase support. Other side chain groups suitable for coupling to the solid phase support include but are not limited to the side chain of aspartic acid, and the succinyl anhydride derivatized ε-amino group of lysine.

The nucleophilic group of the diketopiperazine linkers is protected during synthesis and prior to cleavage of the peptide. In one embodiment of the invention, the cleavage reaction can be controlled at the level of deprotection of the nucleophile. In a specific embodiment, in which the nucleophile is an imino group of iminodiacetic acid or an α-amino group of the linker dipeptide, the protecting group can be Boc, Fmoc, Alloc, Npys, Z, or a modified Z group. As is well known in the art such protecting groups are removable under different conditions, and can be used where removal under such conditions is desired. For example, the Boc protecting group is removed with TFA; the Fmoc protecting group is removed under basic conditions; the Alloc protecting group is removed by hydrogenolysis; the Npys protecting group is removed under reducing conditions, e.g., by treatment with a free —SH group; and the Z protecting group is removed in HBr or acetic acid, or by hydrogenolysis.

In a further embodiment, in which multiple linkers are used, two diketopiperazine type linkers releasable under different conditions are employed. The different linkers have different protecting groups, e.g., Boc on one linker, Npys or Alloc on the other linker, and thus are cleavable after different deprotection procedures.

After deprotection of the nucleophile, the nucleophile can react with the ester carbonyl, releasing the peptide. However, the rate of this nucleophilic attack depends on the pH of the buffer, on the nucleophilicity of the nucleophile, and on the size and type of the ring to be formed. For example, in acidic pH, the electrons of the nucleophile will interact with the Lewis acid. If the nucleophile is an amine, the amine will be protonated. Under these conditions, nucleophilic attack will not occur or it will be very slow. Thus, the diketopiperazine linker requires at most slightly acidic (pH 6–7), preferably neutral (pH 7) or slightly basic (greater than pH 7) conditions to release the peptide within a reasonable period of time. Adjustment of pH is one means provided to control the rate of release of a peptide. In a specific embodiment, the peptide is released rapidly at pH 8.5 when the linker is IDA-IDA, Gly-IDA, and Glu-Pro. In another embodiment, the peptide is released at pH greater than pH 8.5.

The potential of the linker to form a cyclic structure depends very much on the number of atoms in the ring. Cyclization reactions which form a five- or six-membered ring structure, with six-membered rings more favored. Cyclization to form four-membered rings or less, or seven membered rings or more, are not favored.

The rate of cleavage also depends on the inherent nucleophilicity of the nucleophile. This in turn is affected by the neighboring functional groups. Thus, in the example in which the linker is a dipeptide, the side chain of the nucleophilic peptide will primarily determine the relative nucleophilicity of the α-amino group. For example, S-methylcysteine will increase the nucleophilicity of the amino group due to the inductive effect of sulfur in its side chain. On the other hand, the oxidized (sulfoxide or sulfone) form of this amino acid will significantly decrease amino group nucleophilicity.

In a further embodiment, the rate of cleavage is determined by the accessibility of the ester carbonyl. For example, if bulky groups, such as but not limited to secondary and tertiary aryl or alkyl groups, including heteroaryl or hetero-alkyl groups, are located in proximity to the ester carbonyl, the nucleophile may be sterically hindered from attacking the carbonyl. In one embodiment, access to the ester carbonyl is hindered by the presence of a methyl, ethyl, propyl, etc. group in the C1 position next to the oxygen bound to the carbonyl. The reaction rate can be increased, on the other hand, by removing bulky groups in proximity to the ester carbonyl.

In yet a further embodiment, the reaction rate can be affected by altering the propensity of the linker to cyclize. Inclusion of a proline amino acid residue in the second (C-terminal) position of a linker increases the rate of cleavage. Although not intending to be held to any particular theory, this increase in the rate of cleavage corresponds to an increased propensity to cyclize. On the other hand, inclusion of a proline amino acid in the first (N-terminal) position of the linker decreases the rate of cleavage. In a specific example, infra, the linker Glu-Pro cleaves rapidly at pH 8.5, but the linker Pro-Glu cleaves very slowly at this pH. In another embodiment, the linker includes D-amino acids, which are known to cyclize readily. Furthermore, it is known that steric effects determine cyclization potential as well. For example, peptides with amino terminal glycine will cyclize very fast in comparison to peptides with amino terminal valine, which, however, will be still faster cyclizing than a peptide containing the N-terminal sterically demanding aminoisobutyric acid.

It can be readily appreciated by one of ordinary skill in this art, provided with the foregoing teachings, that the diketopiperazine linkers of the invention can include any linker that, by cyclization, can place a nucleophile in proximity to the ester carbonyl for reaction with the carbonyl. Such a strategy is preferred because it does not require an excess of free nucleophile, since each linker includes a nucleophile. IDA linkers are especially preferred.

In one embodiment, the linker is synthesized by forming an ester of the carboxyl group (e.g., of an amino acid or any carboxylic acid) with an short chain (C1 to C6) amino alcohol. The amine group can then be coupled to the carboxyl group of the first amino acid of the peptide chain, using standard peptide synthetic methods. In another embodiment, the side chain of serine or threonine can act as the alcohol, obviating the need for an amino alcohol derivative.

5.1.2. ESTER LINKERS CLEAVABLE AT HIGHER pH

In yet another embodiment, the linker of the invention can contain an ester bond that is susceptible to cleavage by a free nucleophile, e.g., hydroxy ion or ammonia. In a specific example, the linker can be IDA in which the imino group is coupled to a carboxyl, and thus is not free for nucleophilic attack. In another example, the linker can be glutamic acid-propanolamine (in which the amino group of the propanolamine is coupled to the C-terminal carboxyl of the peptide). Other suitable acid groups for linkers include but are not limited to p-(hydroxymethyl)benzoic acid, aspartic acid, and hydroxyacetic acid. Instead of aminoalcohols, derivatives of serine, homoserine and threonine substituted in their OH groups (by formation of the ester bond) may be used.

The ester bond can be cleaved by treatment with a strong base. For example, the bond can be cleaved by treatment with 0.1% sodium hydroxide (NaOH). In another embodiment, the bond can be cleaved by treatment with ammonia in alcohol, preferably methanol or by exposure to gasseous ammonia. A particular advantage of the latter system is that after cleavage, the ammonia and alcohol can be evaporated, leaving the cleaved peptide at neutral pH.

5.1.3. RELEASE OF COMPOUNDS WITH FREE CARBOXY GROUP

In the previous embodiments the release of compound from the double releasable linker based on IDA provides compounds containing the Gly-HOPA attached to it. Since it may be desirable in some instances to release a compound without the hydroxypropylamide of glycine, i.e., having a free carboxy group, a modified IDA-IDA linker is provided that incorporates a second ester linkage. The ester bond is introduced into the linker by attaching a hydroxy acid, e.g. p-hydroxymethylbenzoic acid, serine or 3-hydroxypropylamide of succinic acid to both arms of an IDA-IDA linker. During the first release at pH 8 the DKP is formed and compound with the hydroxy acid linker is released to the solution. Then the beads are separated from the solution by filtration, the pH is brought to about 13 by addition of a strong base, such as NaOH. After incubation for a period sufficient to hydrolyze the ester, typically about 30 min, the base is neutralized so that the pH is suitable for a biological screening assay. Thus, the second release is performed by the use of NaOH as described before and, due to the presence of the second ester bond, it provides directly the desired compound with free carboxy group.

The general structure of a linker of this embodiment that yields compounds with free carboxy groups is:

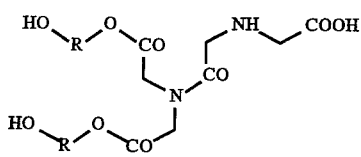

wherein the free carboxy is intended to be attached to the solid phase support and R is carbon or a heterocarbon skeleton that links two hydroxyl groups (e.g., R=—(CH$_2$)$_3$—O—CO(CH$_2$)$_2$—CO—Gly-NH—(CH$_2$)$_3$—). The essential ester bond, for the purpose of the invention is the ester bond closest to the peptide or other test compound to be released.

The chemistry of both releases on model linker is illustrated schematically in FIG. 8.

5.2. MULTIPLE CLEAVABLE LINKERS

In a preferred aspect of the invention, the ester bond-based linkers are combined with other known cleavable linkers to provide for sequential release of peptide from the solid phase support. Such multiple cleavable linkers have been described previously (International Patent Publication No. WO92/00091). The ester bond-based cleavable linkers provide a preferred linker in combination with other selectively cleavable linkers. In a specific embodiment, both the diketopiperazine linker and an ester bond linker cleavable at high pH are combined on a solid phase support.

As can be readily appreciated by one of ordinary skill in the art, there are numerous strategies for attaching several different cleavable linkers to a solid phase support. Preferably the linker is attached to the solid phase support using standard chemical condensation reaction techniques, e.g., reaction of an activated carbonyl on the linker with a free amine or other nucleophile on the solid support. To attach more than one linker, preferably the solid support or handle attached to the solid support is further derivatized with branching lysine groups. Each of the two amine groups on the lysine can be selectively deprotected and coupled with a specific linker or with another lysine, in order to continue branching and attaching additional linkers. In another embodiment, the linker can be reacted such that the concentration of linker is a fraction of the concentration of nucleophile. Thus each linker can be coupled non-quantitatively to the solid support, leaving free nucleophilic groups for coupling to the next linker.

According to the present invention, a number of different linkers can be combined on a single solid phase support in addition to the ester bond linkage based linkers. These include but are not limited to linkers that are acid-sensitive, base-sensitive, nucleophilic-sensitive, electrophilic sensitive, photosensitive, oxidation sensitive or reduction sensitive. Examples of photosensitive (photocleavable) linkers are found in Barany and Albericio (1985, J. Am. Chem. Soc. 107:4936–4942), Wang (1976, J. Org. Chem. 41:32–58), Hammer et al. (1990, Int. J. Pept. Protein Res. 36:31–45), and Kreib-Cordonier et al. (1990, in Peptides—Chemistry, Structure and Biology, Rivier and Marshall, eds., pp. 895–897). Landen (1977, Methods Enzym. 47:145–149) describes using aqueous formic acid to cleave Asp-Pro bonds. Other potential linker groups cleavable under basic conditions include those based on p-(hydroxymethyl) benzoic acid (Atherton et al., 1981, J. Chem. Soc. Perkin I:538–546) and hydroxyacetic acid (Baleaux et al., 1986, Int. J. Pept. Protein Res. 28:22–28). Geysen et al. (1990, J. Immunol. Methods 134:23–33) reported peptide cleavage by a diketopiperazine mechanism. Thus the instant invention provides for "reverse" diketopiperazine linkers used in conjunction with the diketopiperazine release mechanism described by Geysen et al. Preferably different blocking groups are used to block the nucleophiles of the different diketopiperazine linkers. An enzyme may specifically cleave a linker that comprises a sequence that is sensitive or a substrate for enzyme cleavage, e.g., protease cleavage of a peptide; endonuclease cleavage of an oligonucleotide. In certain instances, one may derivatize 10–50% of the resin by substitution with the cleavable linker, and the remaining 50–90% substituted with a noncleavable linker to ensure that enough peptide will remain after cleavage of linker for sequencing. In addition to the cleavable linkers, various standard linkers, i.e., that can be cleaved under standard cleavage conditions, e.g., 50% TFA or HF, can be used to attach the oligomer to solid phase support. Examples of linkers include aminobutyric acid, aminocaproic acid, 7-aminoheptanoic acid, and 8-aminocaprylic acid. Fmoc-aminocaproic acid is commercially available from Bachem California. In a further embodiment, linkers can additionally comprise one or more β-alanines as spacers. Such standard linkers in the multiple linker embodiment of the invention provide for retention of peptide on the solid phase support for subsequent sequencing.

In a preferred embodiment, a safety-catch handle can be used (see Patek and Lebl, 1991, Tetrahedron Lett. 32:3891–4). Such a handle is a substituted benzhydrylamine of the general formula (I):

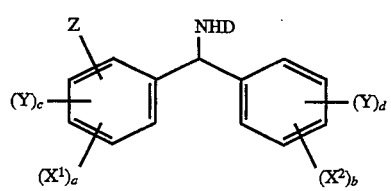

in which a=1 to 3, X$^1$ is [S]R$^1$ or X$^1$ is Z, the X$^1$ groups are in the ortho or para positions of the first benzene ring, and R$^1$ is an alkyl group and in which b=0 to 3, X$^2$ is [S]R$^2$, the X$^2$ groups are in the ortho or para positions of the second benzene ring, and R$^2$ is an alkyl group; and in which Z is R$^3$, OR$^3$ or [S]R$^3$ in any position not occupied by X$^1$ unless X$^1$ is Z, and R$^3$ is an alkyl group comprising a reactive functional group for coupling to a solid phase support, and in which if X$^1$ is Z, Z is [S]R$^3$ in an ortho or para position; and in which c=0 or 1 and d=0 or 1, Y is OR$^4$, and R$^4$ is an alkyl group; and in which [S]is —S—, —SO— or —SO$_2$—; and in which D is H, a protecting group or an N$^\alpha$-protected acyl. As used herein, "alkyl" can be a C$_1$ to C$_{10}$. The safety catch handles can be synthesized as described (Patek and Lebl, supra). For example, hydroxy or mercapto benzophenones can be reacted with ω-haloesters of alkanecarboxylic acids in the presence of fluoride ions. The benzophenone carbonyl is subsequently converted to an amine by routine synthetic methods, e.g., reaction with hydroxylamine to yield an oxime, followed by reduction, e.g., with zinc, to yield benzhydrylamine, or by reductive amination, e.g., by reaction with ammonium formate. Alternatively the benzophenone can be reduced to the alcohol and amidated with an N$^\alpha$protected amino acid amide.

5.2.1. DOUBLE CLEAVABLE LINKER UTILIZING ESTER BOND AND METHIONINE BOND CLEAVAGE

Screening combinatorial libraries using Selectide technology can be performed using either on-bead binding assay or a releasable assay. It may be desirable to combine both methods of screening, i.e., to screen the library for ligand using an on bead binding assay and then confirm the binding of potential ligand in solution. To avoid inadvertent release during the on-bead binding assay a linker is provided that combines an ester linkage suitable for release at high pH and stable at pH 8.5 or below, as described in section 5.1.2, together with a methionine amino acid containing linker. The peptide bond between the carboxy terminal of methionine and a second amino acid can be selectively cleaved by cyanogen bromide accompanied by the formation of a homoserinelactone.

A further application of the methionine containing linkers is the analysis of the compound of interest by mass spectroscopy as such analysis requires cleavage of the compound from the bead.

One example of this type of linker is illustrated by attaching a methionine to a dicarboxylic acid, e.g., glutamic acid, that is linked to the solid-phase support. The ester containing linkage is provided by reaction of the second carboxyl group of glutamic acid with hydroxypropylamine to yield an amide bond. Particularly preferred as the first amino acid to be coupled to the hydroxyl group of the hydroxypropylamine is β-Ala, the presence of which prevents the formation of DKP during the stage of synthesis when there is a free amino moiety of a dipeptide. The construction of a methionine containing linker is illustrated in Example 7.

5.3. USE OF THE LINKER FOR PEPTIDE SYNTHESIS

The linkers of this invention are well suited for attaching a peptide chain to a solid phase support for peptide synthesis. The linkers can be attached to any amino resins via a suitable functional group, e.g., carboxylic acid, on the alkyl group. Attachment of a carboxylic acid functional group to an amine on the resin can proceed according to any of the techniques commonly used for peptide synthesis, e.g., preparation of an OPfp, HOBt or other activated ester, condensation in the presence of a carbodiimide, etc. Suitable solid supports for use in the invention are discussed, supra.

Solid phase peptide synthesis techniques are well known in the art. Simply put, an N$^\alpha$-protected amino acid is activated at the α-carboxyl and coupled with the deprotected N$^\alpha$ of the nascent peptide-linker-solid phase support. The coupling reactions may be accomplished by techniques familiar to those in the art (see, e.g., Stewart and Young, 1984, Solid Phase Synthesis, Second Edition, Pierce Chemical Co., Rockford, Ill.; Fields and Noble, 1990, "Solid phase peptide synthesis utilizing 9-fluorenylmethyloxycarbonyl amino acids," Int. J. Pept. Protein Res. 35:161–214; Geysen et al., 1987, J. Immunol. Methods 102:259–274). The chemistry of coupling, deprotection, and finally cleavage of the peptide from the solid phase support depends on choice of αN-protecting group, which is generally tert-butoxycarbonyl (Boc) or 9-fluorenylmethyloxycarbonyl (Fmoc).

In a preferred embodiment of peptide synthesis using linkers of the invention the completeness of coupling should be assessed. Methods of assessing the completeness of coupling are well known in the art. If the coupling was not complete, the reaction should be forced to completion by a second coupling, e.g., (a) by using a higher concentration of the activated amino acid or a different activation mechanism; (b) with the addition of different or additional solvents; or (c) with the addition of chaotropic salts (see Klis and Stewart, 1990, in Peptides: Chemistry, Structure and Biology, Rivier and Marshall (eds.), ESCOM Publishers, pp. 904–906).

5.4. BIOACTIVITY ASSAYS WITH THE RELEASABLE LINKERS

The cleavable linkers of the invention based on an ester bond linkage are useful for binding assays and biological assays. A portion of peptide from the linker can be released, and its activity detected in situ. The solid phase supports from which peptide of interest was released can then be obtained and the sequence of the peptide remaining on the support determined, as described in International Patent Publication No. WO92/00091. Alternatively, the diketopiperazine linkers of the invention can be used in the traditional methods, such as those described by Geysen et al. (1990, J. Immunol. Methods 134:23–33), with the advantage that the rate of the cleavage reaction can be controlled and the released peptide will not have the diketopiperazine moiety attached.

The ability to control the release rate can be used for biological assays in which the effect of long term slow release of peptide is assayed.

5.4.1. RANDOM PEPTIDE LIBRARIES

In a preferred aspect of the invention, the ester bond linkage based cleavable linkers are used with a random peptide library as described in International Patent Publication No. WO92/00091, published Jan. 9, 1992.

The present invention allows identification of peptide ligands that bind acceptor molecules. As used herein, the term "acceptor molecule" refers to any substance which binds to a peptide ligand. Acceptor molecules may be a biologic macromolecule such as, but not limited to, antibodies, receptors, or viruses. In addition, acceptor molecules may be a chemical compound such as, but not limited to, proteins, carbohydrates, nucleic acids, lipids, drugs, metals or small molecules.

The peptide library of the invention can potentially interact with many different acceptor molecules. By identifying the particular peptide species to which a specific acceptor molecule binds, it is possible to physically isolate the peptide species of interest.

Interaction with acceptor molecules can be detected by competitive binding assays, in which the native ligand of a receptor is labeled. Alternatively, the peptides can be labeled, e.g., by incorporation of a radioactive tracer element, and binding of a labeled peptide to the acceptor molecule detected directly.

The instant invention further provides assays for biological activity of a peptide from a library treated so as to remove any toxic molecules remaining from synthesis, e.g., by neutralization and extensive washing with solvent, sterile water and culture medium. The biological activities that may be assayed include toxicity and killing, stimulation and growth promotion, and physiological change.

According to the present invention, the peptides of the library are selectively cleavable from the solid-phase support using the diketopiperazine linker of the invention, also referred to herein as "bead". In one embodiment, beads are prepared such that only a fraction of peptides are selectively cleavable. The nucleophile of the diketopiperazine linker is deprotected and the library is exposed to mildly basic conditions, e.g., greater than pH 7, such that cleavage of a fraction of peptides occurs. In one embodiment, the library is treated so that 10–90% of the peptides are released. In a more preferred embodiment, 25–50% of the peptides are released. Where all peptides are cleavable, non-quantitative cleavage can be effected by affecting the rate of the cleavage reaction, as described supra, and controlling the concentration and treatment time with the base. After treatment to effect cleavage, the library may be further treated, e.g., by neutralization or addition of a buffer, to make it biologically compatible with the desired assay. In practice, one of ordinary skill would be able to readily determine appropriate cleavage conditions for partial cleavage when all peptides of the library are attached to solid phase by cleavable linkers or bonds. One of ordinary skill would further understand that the relative concentration of released peptide can be affected by varying the cleavage conditions.

Since the beads of the library are immobilized, a concentration gradient of a particular peptide will form. High concentrations of peptide will be found in proximity of the bead from which it was released. Thus, evidence of biological activity of interest, in proximity to a bead, will allow identification and isolation of the bead, and sequencing or other characterization of the peptide. Identification of the peptide is possible because enough will be left on the bead after partial cleavage for sequencing or other characterization. In another embodiment, the beads may be partitioned in microtiter wells (e.g., 10 beads/well) and a percent of peptide released and tested for biological activity, thus eliminating the potential problem of diffusion. As described below, different fractions of peptide may be attached to solid phase support or bead via different cleavable linkers for sequential assays. Within these examples, the term "bead" refers to solid phase support.

The following examples are provided to illustrate how the biological assays may be performed, not as limitations.

(i) A population of cells in single cell suspension is layered over liquid medium or a semi-solid matrix containing a random peptide library. In one embodiment, this procedure is carried out in 96 well microwell tissue culture plates with one or more beads per well plus the cell suspension. In another embodiment, a barrier matrix or "cookie-cutter" is applied to the suspension of cells and the beads of a library to create individual chambers. A proportion of peptide on each bead is linked with a cleavable linker. Sufficient peptide can be released to exert a biological effect while enough peptide still remains linked to the bead for sequencing. The cell suspension may be in solution or may itself be in a semi-solid matrix. After a suitable incubation period, the cell population is examined for growth or proliferation, e.g., by identification of colonies. In another embodiment, the tetrazolium salt MTT (3(4,5-dimethyl-thiazol-2-yl)-2,5-diphenyl tetrazolium bromide) may be added (Mossman, 1983, J. Immunol. Methods 65:55–63; Niks and Otto, 1990, J. Immunol. Methods 130:140–151). Succinate dehydrogenase, found in mitochondria of viable cells, converts the MTT to formazan blue. Thus, concentrated blue color would indicate metabolically active cells. In yet another embodiment, incorporation of radiolabel, e.g., tritiated thymidine, may be assayed to indicate proliferation of cells. Similarly, protein synthesis may be shown by incorporation of $^{35}$S-methionine. Beads releasing peptide which either stimulated or inhibited cell growth would then be recovered and sequenced, with the identified peptide sequences then retested in solution in confirmatory cultures against the indicator cell type.

(ii) In a further embodiment of (i) supra, the beads of a library are distributed into microtiter wells such that each well contains about ten beads. The beads are suspended in solution phase. Sufficient peptide is released from each bead to exert a biological effect while enough peptide remains on the bead for sequencing. The supernatant containing released peptide may be transferred to a replicate plate or left in the wells with the beads. Biological activity, e.g., growth or proliferation of a cell line, is determined. Beads from wells with biological activity are sequenced and each sequence prepared and tested to determine which of the sequences demonstrated biological activity.

(iii) In yet a further embodiment of (ii), supra, peptides are attached to beads such that about ⅓ of peptide can be released in a first step, about ⅓ in a second step, and the remaining ⅓ remain on the bead. Sequential release can result from use of two different cleavable linkers, or by limiting the cleavage agent to release only a portion of the peptide at each step. For the latter, controlled irradiation of a photocleavable linker may be preferred, although carefully timed exposure to a chemical or enzymatic cleavage agent can accomplish partial cleavage. A library of sequentially cleavable peptides is prepared and distributed in wells of microtiter plates such that each well contains more than about 50, and more preferably from about 50 to about 1000, beads per well. The beads are treated so as to cleave about ⅓ of the peptides. Supernatant is assayed for biological activity in a replicate assay. Beads from wells demonstrating biological activity are then suspended and distributed into wells of a microtiter plate so that each well contains about 1 to 10 beads. The beads are treated to release another ⅓ of peptide, and the supernatant assayed for biological activity. Beads from wells demonstrating biological activity are isolated and the attached peptide is sequenced. Where more than one bead is found, all the identified sequences are prepared and individually tested for biological activity. This two step sequential biological assay provides an efficient, powerful method to screen a very large library for peptides with specific biological activity.

(iv) Stimulation of cytokine release may be assayed by adding a single cell suspension immobilized in a semi-solid matrix, e.g., agarose gel. Where a peptide of the invention induces release of cytokine, e.g., lymphokine, growth factor, hormone, etc., presence of the cytokine may be detected by activity of an indicator cell line. Specific assays with an indicator cell line may be made as described in (i), supra. In another embodiment, cytokine released by stimulated cells may be blotted on a membrane, e.g., nitrocellulose, and cytokine detected by immunoassay or a receptor binding assay.

(v) In another embodiment, toxicity of a peptide may be observed. Zones or plaques of na-growth, e.g., of a transformed or cancer cell line layered over a peptide library, would indicate cytotoxic activity. In a particular aspect, two cell populations in a semi-solid matrix may be layered, one over the other. In this way, a cytotoxic peptide specific for the target cell, but not cytotoxic for a bystander cell, could be identified. Such an assay would rapidly identify peptides for use as chemotherapeutic agents.

(vi) Physiologic change may also be assayed. In one embodiment, a myocardial cell suspension is layered over a library. "Beating" of cells stimulated by a peptide may be observed. In another embodiment, up-regulation of a particular enzyme may be assayed by detecting increase in a specific enzyme activity if a suitable substrate is available, such as a chromogen (e.g., MTT, (i), supra), fluorophore, or chemiluminescent. Alternatively, up-regulation of an enzyme may be detected by an immunological assay. In yet a further embodiment, histological techniques may indicate physiological or morphological changes effected by a peptide of the library.

(vii) The present invention provides a method to assay activity of a peptide in a library on polarized cells, e.g., cells with a basolateral and a luminal face. Polar cell cultures may be prepared on a semi-permeable membrane, corresponding to the lumen. A library is added in a semi-solid matrix to the luminal face or the basolateral face. Various effects of a peptide of the invention may be assayed, such as polar transport, proliferation, intercellular communication, etc. In particular, by labelling the peptide, e.g., with a radiolabel or a fluorophore, transportable peptides can be identified. There is a longstanding need in the art for specifically absorbable molecules. In particular, such molecules would be useful for oral or nasal administration of pharmaceuticals, where transport from the luminal surface to the basolateral surface of the epithelium is desired.

It will further be understood by one of ordinary skill in the art that any cell that may be maintained in tissue culture, either for a short or long term, may be used in a biological assay. The term "cell" as used here is intended to include prokaryotic (e.g., bacterial) and eukaryotic cells, yeast, mold, and fungi. Primary cells or lines maintained in culture may be used. Furthermore, applicants envision that biological assays on viruses may be performed by infecting or transforming cells with virus. For example, and not by way of limitation, the ability of a peptide to inhibit lysogenic activity of lambda bacteriophage may be assayed by identifying transfected E. coli colonies that do not form clear plaques when infected.

Methods of the present invention for assaying activity of a peptide of a random library of peptides or a single peptide are not limited to the foregoing examples; applicants envision that any assay system may be modified to incorporate the presently disclosed invention. Applicants envision that such are within the scope of their invention.

5.5. PHARMACEUTICAL USES OF THE CLEAVABLE LINKERS

The selectively cleavable linkers based on an ester bond linkage can be used for the release of pharmaceutical agents in vivo. In one embodiment, the released pharmaceutical agent is a peptide. However, any pharmaceutically active substance that can be bound via an ester bond to the linker can be coupled to the linker for release in vivo. Moreover, since the invention provides for controlling the rate of release of the diketopiperazine linkers of the invention, the present invention allows for varying the release rate, depending on the desired release rate for a molecule of interest.

Moreover, since the present invention provides for release of a free alcohol form of the released entity, and retention of the diketopiperazine on a solid phase support that can be excreted, e.g., after oral administration, the invention provides for release of a proper pharmaceutical agent, uncompromised by a diketopiperazine moiety attached to the pharmaceutical agent.

The present invention will be illustrated by reference to the following examples, which are by way of exemplification and not limitation.

6. EXAMPLE

IMINODIACETIC ACID BASED LINKERS FOR TWO STAGE RELEASE OF PEPTIDES FROM SOLID SUPPORT

Peptides were synthesized on a polymeric support via clearable iminodiacetic acid (IDA) containing linker that allowed two stage independent release of defined portions of peptide into a solution. Peptides were attached to the linker via an ester bond of Fmoc-Gly-propanolamide (PAOH). The ester bond was cleavable by two unique mechanisms, namely (1) by nucleophilic attack of an internal nucleophile resulting in DKP formation and (2) alkaline hydrolysis. Peptides released from both linkers contained identical carboxy termini (hydroxypropylamides, —PAOH, in this example). The most suitable linker contained an IDA-IDA dipeptide motif and peptides were synthesized either on carboxy terminal IDA or each IDA held one peptide.

The synthesis and release of model peptide Leu enkephalin is described. The IDA linker of this example provides for two stage release was designed for and is particularly useful in testing "peptide libraries" consisting of millions of peptides, since it allows to screen peptides for interaction with given acceptor in solution.

Since ordinarily peptides are written out in the N-terminal to C-terminal direction, in the schemes and formulae presented herein, arrows (←) indicate a reverse (C-terminal to N-terminal) orientation.

6.1. MATERIALS AND METHODS

Amino acid derivatives were purchased from Advanced ChemTech, Kentucky, and used without purification. DCC, DIEA, were obtained from Aldrich (Milwaukee); HOBT and BOP were obtained from Propeptide (SNPE Vert-le-Petit, France). TLC were performed on precoated silica gel G plates Whatman (Kent, England) Silica Gel UV$_{254}$ using the solvent systems described. Melting points were determined on a Kofler block and are uncorrected. $^1$H NMR spectra were recorded on a General Electric QE 300 Instrument. All spectra are reported in ppm relative to tetramethylsilane ($\delta$) using either CDCl$_3$ or CD$_3$SOCD$_3$ as solvents. UV/VIS absorption spectra were recorded on a Hewlett-Packard HP8452A Diode-Array spectrophotometer using 1-cm quartz cuvette. Both analytical and preparative HPLC were carried out on a modular Spectra Physics system using Vydac (0.46×250 mm, 5 µm, flow 1 ml/min) and Vydac (10×250 mm, 10 µm, flow 3 ml/min) C-18 columns, respectively.

6.1.1. PREPARATION OF IDA LINKERS tert.Butyloxycarbonyliminodiacetic acid (Boc-IDA); (1)

A solution of iminodiacetic acid 30.0 g (225 mmol) in 1N NaOH (225 ml) and dioxane (200 ml) was stirred and cooled in an ice-water bath. Di-tert-butyl pyrocarbonate (53.9 g, 247 mmol) was added in several portions and stirring was continued at room temperature for 1 hr. Dioxane was evaporated in vacuo, covered with a layer of ethyl acetate (100 ml) and acidified with saturated solution of KHSO$_4$ to pH 2–3. The aqueous phase was extracted with ethyl acetate (3×150 ml). Combined acetate extracts were washed with water (100 ml), dried over anhydrous MgSO$_4$ and evaporated in vacuo. The product was crystallized from solvent mixture of ethyl acetate and petroleum ether. Yield 47.0 g (90%).

tert.Butyloxycarbonyliminodiacetic acid anhydride; (2)

To a solution of Boc-IDA (10.0 g, 43 mmol) in a mixture of dichloromethane (280 ml) and DMF (5 ml), dicyclohexylcarbodiimide (9.76 g, 47.3 mmol) was added. After stirring 2 hours dicyclohexylurea was allowed to crystallize at 4° C. (in a refrigerator). The byproduct was filtered off and after concentration in vacuo crystallization of residual dicyclohexylurea was repeated. Filtrate was evaporated to dryness and crystallized from solvent mixture of ethyl acetate and petroleum ether. Yield 5.7 g (62%); $^1$H-NMR (300 MHz, DMSO-d$_6$, 25° C.) $\delta$: 1.42 (s, 9H, BOC), 4.38 (s, 4H, CH$_2$).

Boc-N(CH$_2$COOH)—CH$_2$—CO-Pro-O—(CH$_2$)$_3$—NH<-Gly<-Fmoc (3)

To a solution of tert-butyloxycarbonyl-iminodiacetic acid anhydride (0.62 g, 2.8 mmol) in DMF (3 ml), Pro-O(CH$_2$)$_3$NH<-Gly<-Fmoc (0.76 g, 1.7 mmol) in DMF (10 ml) was added. The amino component was prepared from the corresponding trifluoroacetate as follows: TFA, Pro-O(CH$_2$)$_3$NH<-Gly<-Fmoc was dissolved in ethyl acetate and extracted into aqueous 1M hydrochloric acid. The aqueous phase was then adjusted to pH 9 by adding a saturated solution of Na$_2$CO$_3$ and immediately extracted with chloroform at 5° C. After drying over MgSO$_4$, solvent was evaporated to dryness. The reaction mixture was stirred for 6 hrs and then evaporated to dryness. The residue was dissolved in methanol and precipitated by adding diethylether to remove remaining Boc-IDA anhydride. The crude product that was obtained was crystallized from a solvent mixture of ethyl acetate and petroleum ether. Yield 0.63 g (57%); $^1$H-NMR (300 MHz, DMSO-d$_6$, 25° C.) $\delta$: 1.35 (s, 9H, BOC), 1.71 (m, 2H, PA C$^\delta$H$_2$), 1.85, 2.14 (m, 2H, Pro C$^\delta$H$_2$), 1.91 (m, 2H, Pro C$^\gamma$H$_2$), 3.13 (m, 2H, PA C$^\gamma$H$_2$), 3.58 (d, 2H, Gly C$^\alpha$H$_2$), 3.75–4.16 (m, 4H, IDA), 4.05 (m, 2H, PA C$^\alpha$H$_2$), 4.32 (m, 1H, Pro C$^\alpha$H), 4.18–4.32 (m, 3H, Fmoc OCH$_2$—CH—), 7.47 (t, 1H, Gly NH), 7.33–7.84 (m, 8H, Fmoc), 7.85 (t, 1H, PA NH).

Boc-N(CH$_2$—COOH)—CH$_2$COO(CH$_2$)$_3$—NH<-Gly<-Fmoc; (4)

Boc-IDA (4.66 g, 20 mmol) was dissolved in 50 ml of DCM:DMF (10:1) mixture, DIC (3.14 ml, 20 mmol) was added, the reaction mixture stirred for 30 min, the solution of Fmoc-Gly-OPA (7.08 g, 20 mmol) and dimethylaminopyridine (0.48 g, 2 mmol) was added, and the reaction mixture stirred overnight. DMF and DCM were evaporated under reduced pressure, the oily residue was dissolved in 100 ml of AcOEt, extracted 3 times with water, 5% aqueous HCl, water, and saturated solution of NaHCO$_3$. NaHCO$_3$ extracts were combined, acidified with aqueous HCl, the product was extracted three times to AcOEt, combined AcOEt extracts washed with saturated solution of NaCl, dried with anhydrous MgSO$_4$, and AcOEt was evaporated under reduced pressure. Yield 6.2 g (55%), single spot of tlc, Rf 0.37. NMR showed the expected signals.

HN(CH$_2$—CO—O—(CH$_2$)$_3$—NH<-Gly<-Fmoc)$_2$, HCl; (5)

A solution of Fmoc-Gly-PAOH (7.08 g, 20 mmol) in 30 ml DMF was added to a solution of Boc-IDA (2.33 g, 10 mmol); HOBt (2.7 g, 20 mmol), and DIC (3.14 ml, 20 mmol) in 30 ml DMF and dimethylaminopyridine (0.48 g, 4 mmol) were added, and the reaction mixture was stirred at RT for 5 h. DMF was evaporated under reduced pressure, the oily residue dissolved in 100 ml of AcOEt, filtrated, extracted 3 times with water, 5% aqueous HCl, water, saturated solution NaHCO$_3$, water, and saturated solution NaCl in water. The organic layer was dried by anhydrous MgSO$_4$ and AcOEt was evaporated under reduced pressure. Yield 7.2 g (80%) of crispy foam, Rf 0.55 (contains two impurities with Rf 0.37 and 0.62). The product was dissolved in 30 ml DCM, 30 ml of TFA was added, and the reaction mixture was kept 30 min at RT. DCM and TFA were evaporated under reduced pressure, the oily residue was dissolved in AcOEt, and washed 3 times with water and saturated solution of NaHCO$_3$. After extraction with solution of Na$_2$CO$_3$, three layers were formed. The bottom layer containing the product was separated, acidified by shaking with 5% HCl, dissolved in chloroform, dried by anhydrous MgSO$_4$, concentrated to a small volume and poured into a large excess of ether. Precipitate was collected, washed with ether and dried. Yield 5.4 g, (64%) of crispy foam, single spot on tlc, Rf 0.28 in CHCl$_3$:MeOH:AcOH (90:9:1); $^1$NMR (300 MHz, DMSO-d$_6$, 27° C.) $\delta$: 1.78 (m, 2H, PA C$^\beta$H2), 3.17 (m, 2H, PA C$^\gamma$H$_2$), 3.60 (d, 2H, Gly CH$_2$), 4.01 (m, 4H, IDA CH$_2$), 4.18 (m, 2H, PA C$^\alpha$H$_2$), 4.19–4.34 (m, 3H, Fmoc OCH$_2$CH), 7.52 (t, 1H, Gly NH), 7.33, 7.43, 7.72, and 7.90 (m, 8H, Fmoc aromatic H), 7.96 (t, 1H, PA, NH).

Boc-N(CH$_2$—COOH)—CH$_2$—CON(CH$_2$—COO—(CH$_2$)$_3$—NH<-Gly<Fmoc)$_2$; (6)

Boc-IDA (2.33 g, 10 mmol) was dissolved in 50 ml of DCM:DMF (10:1), DIC (1.57 ml, 10 mmol) was added and the reaction mixture stirred for 30 min. Then the solution of HN(CH$_2$—CO—O—(CH$_2$)$_3$—NH<-Gly<Fmoc)$_2$.HCl (5) (8.4 g, 10 mmol) in 50 ml DMF was added, the pH was brought to about 8 by DIEA, and the reaction mixture was stirred at RT for 1 h. DMF and DCM were evaporated under reduced pressure, the oily residue dissolved in 100 ml of AcOEt and extracted 3 times with water, 5% aqueous HCl, water, and a saturated NaHCO$_3$ solution. NaHCO$_3$ extracts were combined and acidified with aqueous HCl. The product was extracted three times into AcOEt, dried with anhydrous MgSO$_4$, and AcOEt was evaporated under reduced pressure. The oily residue was triturated with ether and the product crystallized. Yield 6.8 g (67%); single spot on tlc, Rf 0.28 in CHCl$_3$:MeOH:AcOH (90:9:1); $^1$NMR (300 MHz, DMSO-d$_6$, 27° C.) δ: 1.36 (s, 9H, Boc), 1.75 (m, 2H, PA C$^\beta$H$_2$), 3.16 (m, 2H, PA C$^\gamma$H$_2$), 3.60 (d, 2H, Gly CH$_2$), 3.76–4.23 (m, 8H, IDA CH$_2$), 4.11 (m, 2H, PA C$^\alpha$H$_2$), 4.19–4.34 (m, 3H, Fmoc OCH$_2$CH), 7.49 (t, 1H, Gly NH), 7.34, 7.42, 7.72, and 7.89 (m, 8H, Fmoc aromatic H).

6.1.2. GENERAL PROTOCOL FOR SOLID PHASE SYNTHESIS

Tentagel (substitution 0.23 mequiv. NH$_2$/g) was subjected to solid phase synthesis using the following general protocol

| step | reagent | time |
| --- | --- | --- |
| 1 | 5% DIEA/DMF | 2 × 5 min |
| 2 | DMF wash | 10 × 2 min |
| 3 | coupling linker (or Boc-AA or Fmoc-AA) using BOP chemistry | until Kaiser test is negative |
| 4 | repeat step 2 | |
| Boc group deprotection: | | |
| 5 | DCM | 2 × 5 min. |
| 6 | TFA/DCM/anisole (10/10/1) | 1 × 30 min |
| 7 | repeat step 5 | |
| 8 | 5% DIEA/DCM | until pH-8 |

| step | reagent | time |
| --- | --- | --- |
| Fmoc group deprotection: | | |
| 10 | DMF wash | |
| 11 | 50% piperidine/DMF | 10 min |
| 12 | repeat step 2 | |

Fmoc release was quantified by measuring the absorbance (302 nm) of piperidine solution and combined washes.

Boc-IDA(Fmoc-Trp-Gly-PAO<-Pro)-TG (7)

TentaGel (0.2 g, substitution 0.23 mequiv. NH$_2$/g) was preswollen in DCM, DMF (5 ml plastic syringe equipped with polypropylene frit). The linker Boc-IDA(Fmoc-Gly-PAO<-Pro)OH (0.1 g, 0.15 mmol) in DMF (2 ml), BOP (0.066 g, 0.15 mmol), HOBT (0.025 g, 0.15 mmol), and DIEA (0.026 ml, 0.15 mmol) was coupled to the TentaGel according to the general protocol. After Fmoc deprotection, Fmoc-Trp (0.059 g, 0.138 mmol) in DMF (2 ml) activated by BOP (0.061 g, 0.138 mmol), HOBT 0.019 g, 0.138 mmol, and DIEA 0.024 ml, 0.138 mmol) was coupled to the glycine carboxylate.

Boc-Gly-IDA(Fmoc-Trp-Gly<-PAO)-TG (8)

Boc-IDA-(Fmoc-Gly-PAO)OH (0.019 g, 0.035 mmol) in DMF (1 ml) activated by BOP (0.015 g, 0.035 mmol), HOBT (0.05 g, 0.035 mmol), and DIEA (0.006 ml, 0.035 mmol) was attached to TentaGel (0.05 g, substitution 0.23 mequiv. NH$_2$/g) in the same manner as described for (7), above. After Boc group removal and attaching Boc-Gly (0.006 g, 0.035 mmol) activated by BOP (0.015 g, 0.035 mmol), HOBT (0.005 g, 0.035 mmol), and DIEA (0.006 ml, 0.035 mmol) in DMF (1 ml), the Fmoc group was removed and Fmoc-Trp (0.015 g, 0.035 mmol) in DMF (1 ml) activated by BOP (0.015 g, 0.035 mmol), HOBT 0.005 g, 0.0335 mmol, and DIEA 0.006 ml, 0.035 mmol) was coupled to Boc-Gly-IDA-(H-Gly-PAO)-TG.

Synthesis of double cleavable linker resin construct I with different peptides on each cleavable arm (9)

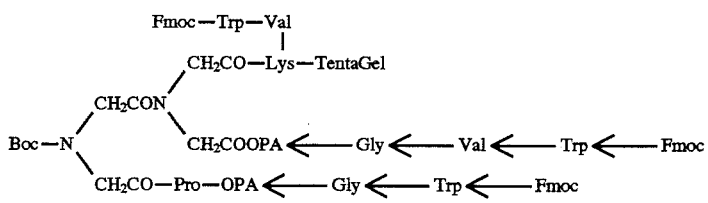

Boc-Lys (Fmoc) (0.023 g, 0.045 mmol) activated by BOP (0.021 g, 0.045 mmol), HOBT (0.006 g, 0.045 mmol), and DIEA (0.009 ml, 0.045 mmol) was coupled to Tentagel (20 mg, substitution 0.23 mequiv. $NH_2$/g). After Boc group removal, Boc-IDA-(Fmoc-Gly-PAO)OH (4) (0.025 g, 0.045 mmol) activated in the same way as Boc-Lys (Fmoc) was coupled to Lys (Fmoc)-TG. Fmoc group removal allowed coupling of Fmoc-Val (0.031 g, 0.090 mmol), in the presence of BOP (0.040 g, 0.090 mmol), HOBT (0.012 g, 0.090 mmol), and DIEA (0.016 ml, 0.090 mmol). The Boc group of iminodiacetic acid was removed and after neutralization as described in the general protocol, Boc-IDA-(Fmoc-Gly-PAO-Pro)OH (3) (0.030 g, 0.45 mmol), activated in the same way as Boc-Lys(Fmoc), was coupled. The final Fmoc deprotection was followed by Fmoc-Trp (0.019 g, 0.045 mmol) (BOP activation as described above) coupling. Synthesis of double cleavable linker-resin construct II with different peptides on each cleavable arm (10)

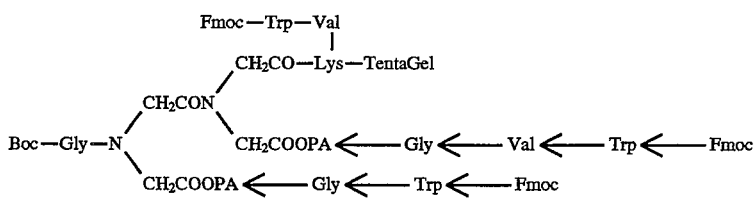

Tentagel (0.060 g, substitution 0.23 mequiv. $NH_2$/g) was subjected to solid phase synthesis using the same protocol as described for linker I with the exception of employing Boc-IDA-(Fmoc-Gly-PAO)OH (4) (0.023 g, 0.042 mmol), BOP (0.019 g, 0.042 mmol), HOBT (0.006 g, 0.042 mmol), and DIEA (0.007 ml, 0.042 mmol) instead of Boc-IDA-(Fmoc-Gly-PAO-Pro)OH in the coupling of the second arm. This was followed by Boc deprotection and subsequent Boc-Trp coupling.
Boc-N[$CH_2$—CON($CH_2$—CO-Lys(Fmoc)-TG)—$CH_2$—COO—($CH_2$)$_3$—NH<-Gly<-Fmoc]-$CH_2$—COO—($CH_2$)$_3$—NH<-Gly<-Fmoc (11)
Boc-N($CH_2$—COOH)—$CH_2$—COO—($CH_2$)$_3$—NH<-Gly<-Fmoc (4) (0.57 g 1 mmol), using BOP (0.44 g, 1 mmol), HOBt (0,135 g, 1 mmol), and DIEA (0.175 ml, 1 mmol), was attached to Lys (Fmoc)-TG (2 g, 0.2 mmol $NH_2$/g, see peptide resin (9) according to the general protocol. The Boc group was deprotected and the second arm (again compound (4)) was coupled by the same procedure.
Boc-N($CH_2$—CO-Lys(Fmoc)-TG)—$CH_2$—CON($CH_2$—COO—($CH_2$)$_3$—NH<-Gly<-Fmoc)$_2$(12)
Boc-N($CH_2$—COOH)—$CH_2$—CON($CH_2$—COO—($CH_2$)$_3$—NH<-Gly<-Fmoc)$_2$ (6) (1.2 g, 1 mmol), BOP (0.44 g, 1 mmol) HOBt (0.135 g, 1 mmol), and DIEA (0.175 ml, 1 mmol) was attached to Lys (Fmoc)-TG (2 g, 0.2 mmol $NH_2$/g, see protocol for peptide resin compound (9)) according to the general protocol.
Boc-N($CH_2$—CO—TG)—$CH_2$—CON($CH_2$—COO—($CH_2$)$_3$—NH<-Gly<-CO—($CH_2$)$_2$—CO—NH—($CH_2$)$_3$—O<-Gly<-Trp<-Fmoc)$_2$ (13)
The linker was constructed as follows: Boc-N($CH_2$—COOH)—$CH_2$—CON($CH_2$—COO—($CH_2$)$_3$—NH<-Gly<-Fmoc)$_2$ (Linker 6) was coupled to TG, Fmoc groups were removed and the resin was reacted with succinic anhydride in DMF (5 molar excess) for 2 h. After washing the resin 5 times with DMF, the carboxyl group on the resin was activated by HBTU/DIEA and 3 molar excess of HOPA was added. The reaction was allowed to proceed overnight, the resin was washed 5 times with DMF and the coupling was repeated under the same conditions and the resin was washed 5 times with DMF.

The model compound was constructed as follows: Fmoc-Gly was preactivated by DIC/HOBT and added in 5 molar excess to the resin with linker, the esterification was catalyzed by DMAP. After overnight reaction the resin was washed 5 times with DMF, Fmoc group was removed and Fmoc-Trp, activated via DIC/HOBT, was coupled in 3 molar excess. The resin was washed 5 times with DMF, Fmoc group cleaved, resin washed by DMF and DCM, and Boc group from linker cleaved by mixture K. The resin was washed by TFA, DCM, MeOH and dried.

Control release from linker V: The procedure for the first release was essentially the same as described for the control release from linker IV, see section 6.2 infra. The structure of product from the first released Trp-Gly-O—($CH_2$)$_3$—NH—CO—($CH_2$)$_3$CO—NH—($CH_2$)$_3$—OH, was confirmed by MS. The solution was then alkalized by 2N NaOH, after 30 min pH was brought to ca 5 by 1N HCl and the structure of product, Trp-Gly-OH, was again confirmed by MS. The second release was performed by the same way as described and the product was quantified and its structure was confirmed by MS.

6.1.3. SYNTHESIS OF DOUBLY CLEAVABLE LEU ENKEPHALIN

Leu enkephalin peptide (YGGFL) was synthesized on the arms of double cleavable linker IV using the standard Fmoc tBu protocol.

6.1.4. Trp-Gly-PAOH CONTROL RELEASE

The Fmoc group was removed from the double cleavable linker-resin construct according to the general protocol, and Fmoc-Trp activated by BOP chemistry was coupled to all three arms. After DMF wash, the Fmoc group and Boc group were removed sequentially according to the general protocol. The deprotected peptide-resin was washed with DCM (10 times), MeOH (5 times) and dried/lyophilized overnight. Dried peptide-resin (about 5 mg) was treated with bicarbonate buffer at pH 8.3 for 3 hrs. Trp-Gly-PAOH release was quantified by measuring the absorbance of Trp (280 nm). The resin was washed thoroughly with water and incubated with 0.5% NaOH for 2 h. The absorbance of released Trp-Gly-PAOH in the solution was read at 280 nm.

6.1.5. PEPTIDE RELEASE KINETICS

Peptide-resin (5 mg) was added to stirred buffer solution at pH 8.3 (100 mM bicarbonate buffer) in a cuvette of a scanning UV spectrometer (Hewlett-Packard, HP 1050 HPUV). Using a 4 sec interval, multiple scans of the UV spectrum from 200–500 nm were obtained and the kinetics of Trp-Gly-PAOH release was followed.

6.2. RESULTS

Starting from tert-butyloxycarbonyliminodi-acetic acid (Boc-IDA), Boc-IDA-Pra-OPA<-Gly<-Fmoc was prepared via opening the Boc-IDA anhydride by nucleophilic attack of Pro-OPA<-Gly<-Fmoc. Boc-IDA-OPA←-Gly←-Fmoc was prepared via opening Boc-IDA anhydride by nucleophilic attack of HOPA←Gly←Fmoc. This reaction is shown in Scheme 1:

A model peptide-resin construct (7) was assembled and after deprotection the model dipeptide was released and kinetics were followed. The reaction kinetics of release of the peptide Trp-Gly-PAOH are shown in FIG. 1.

Double cleavable linker-resin construct I is shown below:

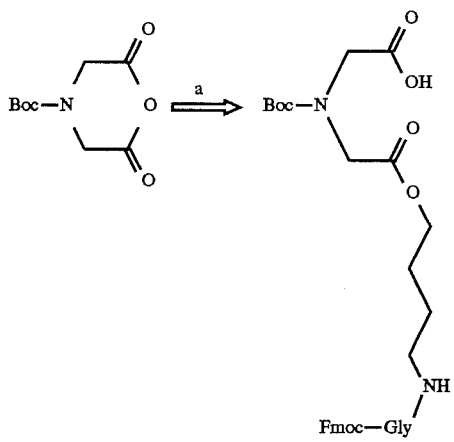

a: Fmoc—Gly—PAOH, DMAP

Double cleavable linker-resin construct I

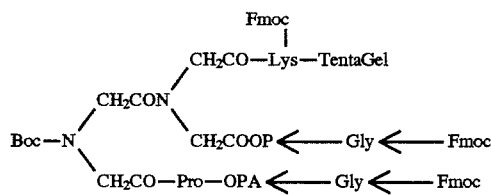

This linker was built using two different arms that were differentiated by having different model peptides synthesized on them. The reaction kinetics of the release at pH 8.3 are shown in FIG. 2. The first release occurs at pH 8.5 (FIG. 2A); the second release occurs at pH 13.2 (FIG. 2B).

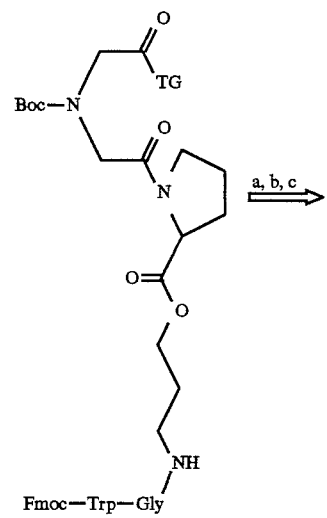

a: 50% piperidine/DMF;
b: TFA/DCM/TA,
c: buffer pH 8.5

The mechanism of the reaction whereby the release is accompanied by the generation of hexahydropyrrolo(1,2-a)pyrazine-1,4-dione (HHPPD) is shown in Scheme 2, supra. HPLC analysis of the released peptides revealed that in addition to the above mechanism there was unexpectedly a second mechanism of heterocycle formation. The formation of cyclic IDA-IDA diketopiperazine was shown to be faster than cyclic HHPPD formation. Thus, during the first release (by heterocycle formation), the peptide from the IDA arm, which was expected to be released by alkali hydrolysis, was released at pH 8.3 instead. The peptide from the proline arm could be released at pH 13.2.

From the results with I, a second IDA-based linker, II, was designed and synthesized. This linker is shown below:

Double cleavable linker-resin construct II

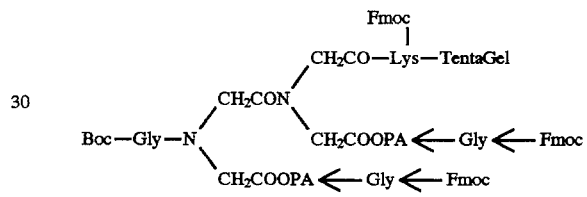

An advantage of this linker is that each branch is identical in structure but each releases peptide through a unique mechanism. The reaction mechanism is shown in Scheme 3:

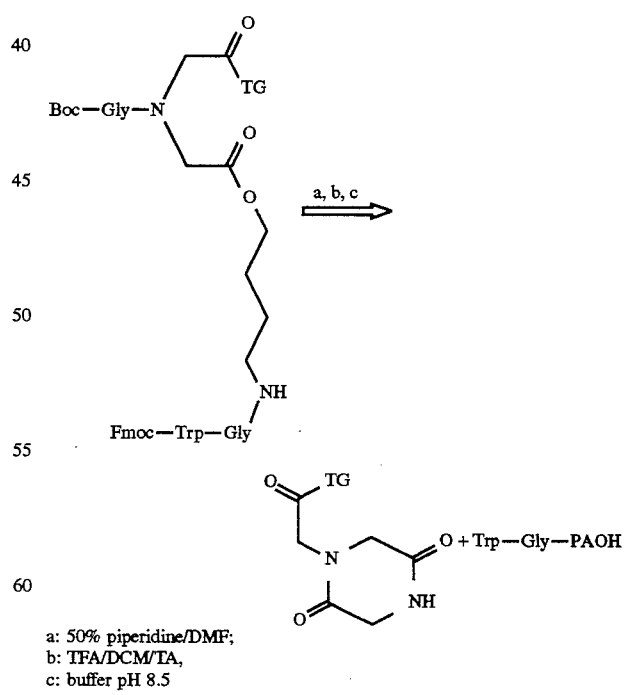

a: 50% piperidine/DMF;
b: TFA/DCM/TA,
c: buffer pH 8.5

Further simplification of the linker structure by omitting Boc-Gly lead to another version of double cleavable linker (III) shown below:

Double cleavable linker-resin construct III

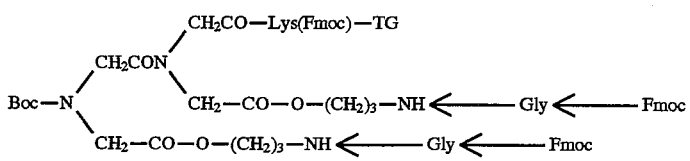

Variation on this structural theme results in design of yet another double cleavable linker (IV), shown below:

Double cleavable linker-resin construct IV

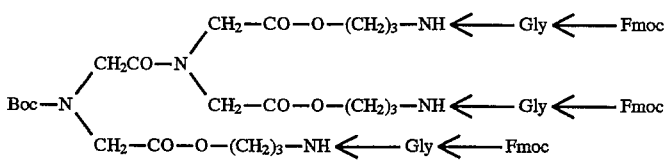

Table 1 summarizes release of peptide from various linkers.

TABLE 1

| Linker-TG | Fmoc release (mmol/g) | 1st peptide release (mmol/g) | 2nd peptide release (mmol/g) |
|---|---|---|---|
| (7) | 0.20 | 0.20 | |
| (8) | 0.13 | 0.13 | |
| (9) | 0.153 | 0.055 | 0.073 |
| (10) | 0.142 | 0.053 | 0.083 |
| (11) | 0.230 | 0.083 | 0.092 |
| (12) | 0.220 | 0.088 | 0.081 |

Note. Fmoc release from Boc-Lys(Fmoc)-TG was 0.2 mmol/g and this value was subtracted from Fmoc reading of the whole linker-resin construct to obtain an estimate of the amount of releasable peptide.

Boc-IDA(H-Trp-Gly-PAO)-TG (6 mg) was treated with 20% piperidine in DMF to test its stability in the presence of this weak base. Fmoc-Trp-Gly-PAOH release was quantified by measuring the absorbance (302 nm) of the piperidine releasate solution. The stability of the ester bond linkage is demonstrated in Table 2.

TABLE 2

| Time (hrs) | released peptide (%) |
|---|---|
| 0.5 | 0.26 |
| 1 | 0.65 |
| 3 | 1.01 |
| 5 | 1.10 |
| 36 | 3.7 |

Leu-enkephalin was released from the double cleavable link construct IV in two steps. The first release at pH 8.3 yielded 65 mmol of peptide per gram of resin. The second release at pH 13.2 yielded 62 mmol/g. Analytical HPLC showed the same peak for both released peptides. The purity of both released peptides was greater than 98%.

6.3. DISCUSSION: LINKERS BASED ON AN IDA-IDA MOTIF

The dipeptide motif IDA-IDA was found particularly suitable for designing double cleavable linkers. The IDA-IDA dipeptide is prone to DKP formation, since it provides three carboxyl groups, one on the amino terminal IDA and two on the carboxy terminal. To construct a double cleavable linker, two carboxyl groups are needed for derivatization and subsequent peptide building. There are two possible ways to attach two Fmoc-Gly-PAOH's to carboxyl groups. Fmoc-Gly-PAOH's are either coupled to both carboxyls of carboxy terminal IDA (linker IV), or each IDA bears one Fmoc-Gly-PA (linker III). In any case there is one free carboxyl group that serves for connecting the linker to the solid support (e.g., via Lys, which itself provides one extra amino group for synthesis of a third copy of peptide, nonreleasable, which non-releasable peptide can be used for sequencing by Edman degradation).

The whole linker IV was synthesized in solution. Both carboxyl groups of Boc-IDA were activated by DIC and HOBt and allowed to react with Fmoc-Gly-PA in the presence of catalyst dimethylaminopyridine. After removing the Boc protecting group by TFA the free base was used to open preformed cyclic anhydride of Boc-IDA. In this case both Fmoc-Gly-PA's are chemically indistinguishable and the first peptide is cleaved via cyclization and DKP formation from either of the two arms. The DKP formed bears on one nitrogen the second copy of peptide.

Figure 4A:
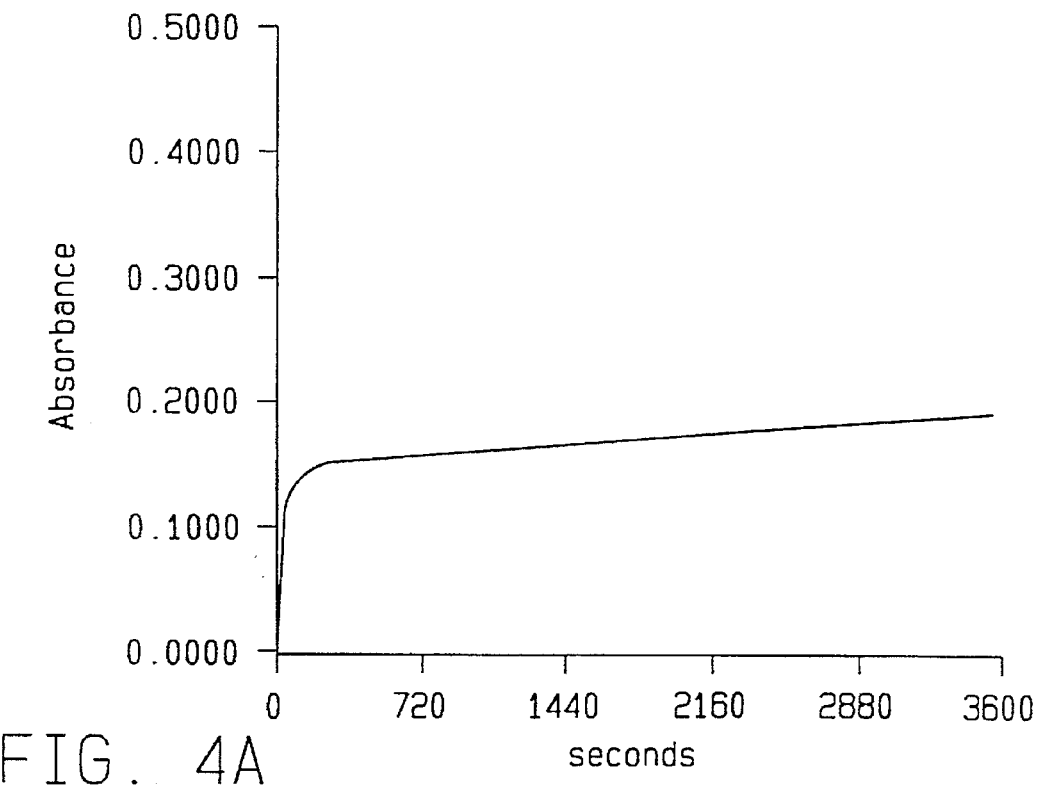
Figure 4B:
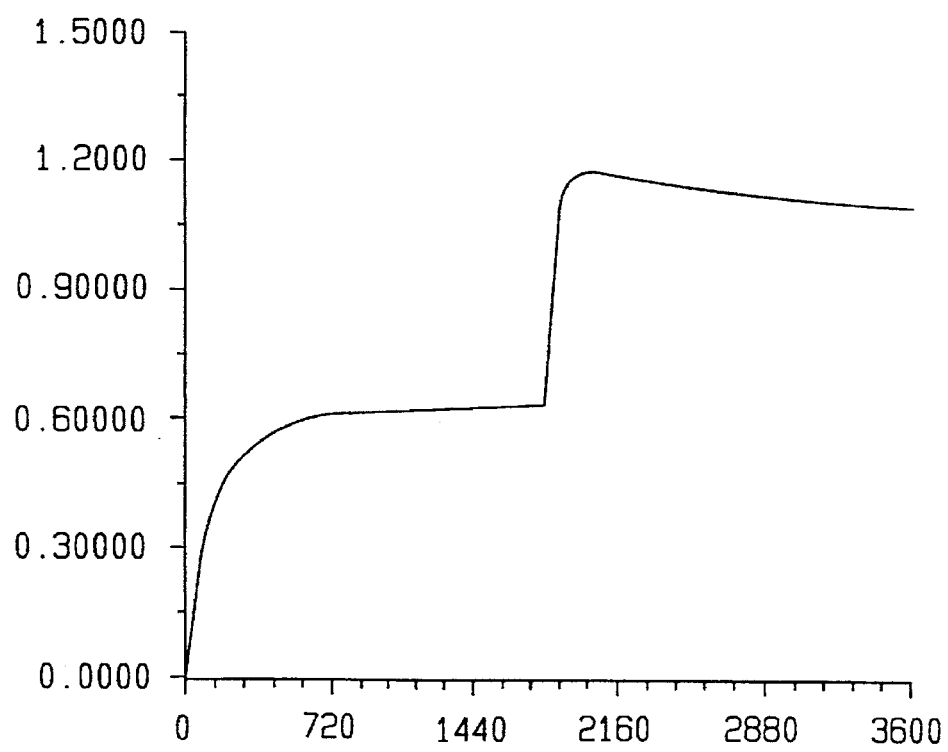
Figure 4C:
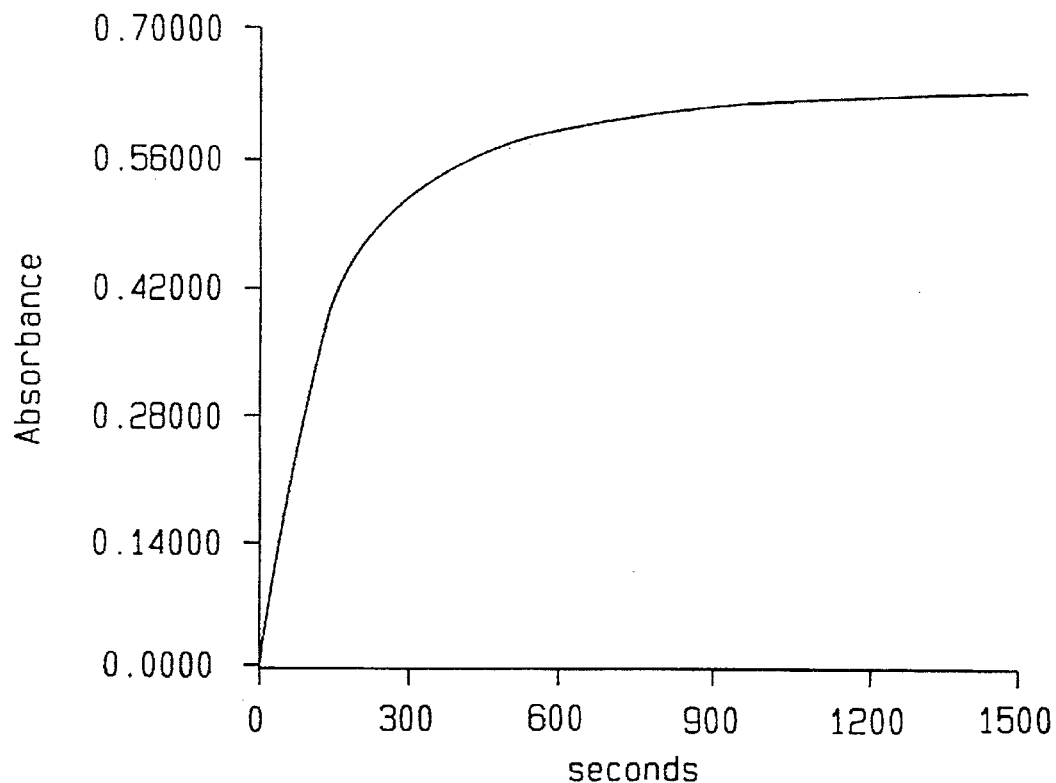
Figure 4D:
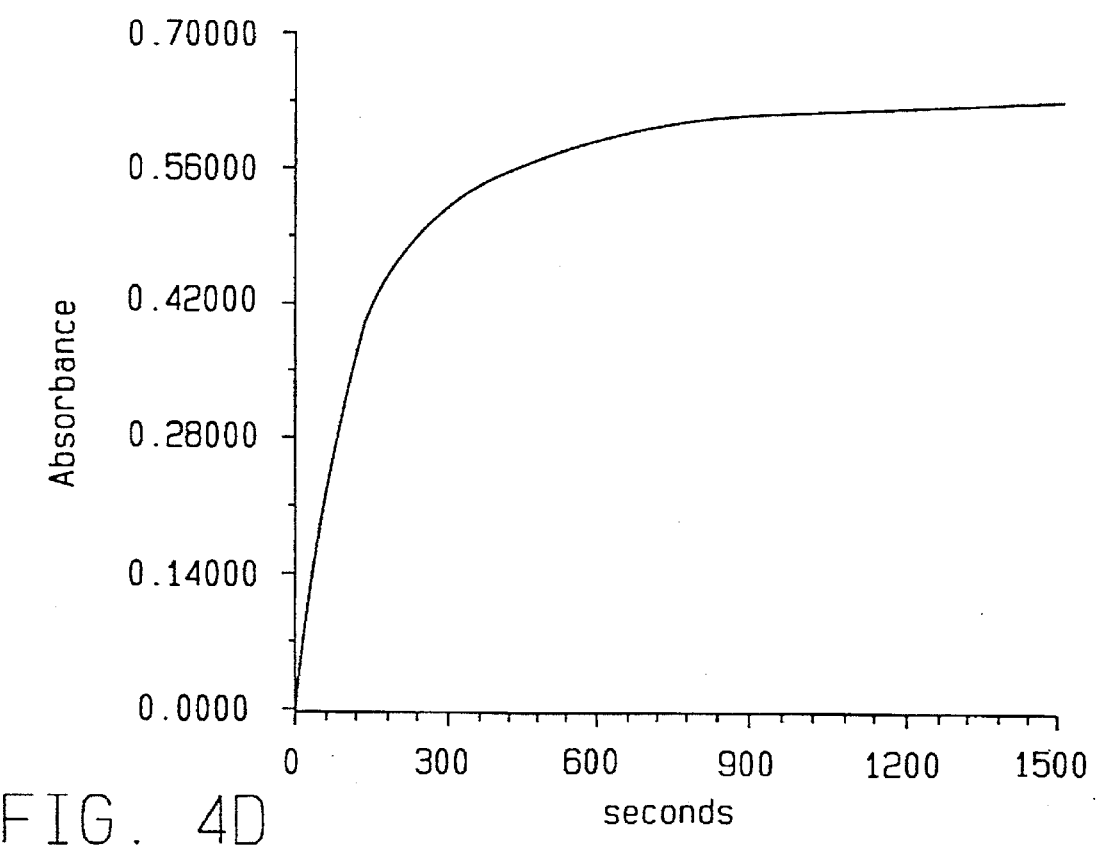

Linker III can be viewed as being composed of two identical building blocks. Boa-IDA anhydride was prepared and opened by Fmoc-Gly-PA resulting in monosubstituted Boc-IDA. Coupling of this product to a solid support, removal of the Boc group and repeated coupling of the same Boc-IDA derivative resulted in the synthesis of desired linker III. When assembled together those two identical building blocks provide us with entirely different reactivities of their esters. After removing the Boc protecting group and adjusting pH, the IDA-IDA dipeptide forms DKP almost instantly, releasing the peptide from the arm that has reacted in the cyclization reaction. The reaction kinetics for release from this peptide were measured at pH 4.0 (FIG. 4A), pH 6.5 (FIG. 4B), pH 8.3 (FIG. 4C). Two-step release (at pH 8.5, then pH 13.2) is shown in FIG. 4D. The second arm retained a peptide for release with alkaline hydrolysis.

This type of linker also provides the possibility for releasing different peptides in each of two steps of release. By separately deprotecting the peptide chain extension portion of the respective arms of the linker, different peptide syntheses can be performed. After coupling the first arm, the Fmoc group is removed and the peptide that is intended to be released in the first step (DKP formation) is synthesized (its amino terminus being protected by the Boc protection strategy). However, the imino group of IDA has to be protected by a more acid labile group, such as Ddz or Bpoc, which allows its smooth cleavage without affecting the side-chain protection in the first peptide. After removing the Ddz/Bpoc group from IDA, the second arm is coupled, the Fmoc group is removed and the second peptide is assembled on the free amino group of Gly.

7. EXAMPLE

METHIONINE CONTAINING LINKERS
γ-(3-hydroxypropylamino)methionylglutamic acid-TG (14)

The structure of a methionine containing linker is given below:

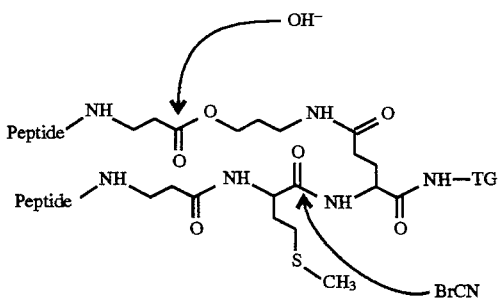

Assembly of the linker on TentaGel:

Fmoc-Glu(OtBu) was activated by DIC/HOBt and coupled to TG (0.2 mmol of amino groups per g of resin) in 3 molar excess. The Fmoc group was cleaved, resin washed 5 times with DMF and Fmoc-Met was coupled. The tBu was removed by exposure to TFA. After washing the resin 5 times with DMF, the carboxyl group on the resin was activated by HBTU/DIEA and 3 molar excess of HOPA was added. Thereafter, the Fmoc group was removed and Fmoc-β-Ala was coupled to both amino and hydroxyl groups on resin via DIC/HOBT activation and catalysis by DMAP overnight and recoupled via symmetrical anhydride. After washing the resin with DMF, the Fmoc group was removed and the absorbance of the solution after deprotection measured and the Fmoc release quantified—Quantification of Fmoc release, 0.38 mmol/g showed almost quantitative coupling of β-Ala.

This linker was used in the solid-phase synthesis of a pentapeptide as described above. The product was cleaved from both arms and its purity was determined by analytical HPLC, the structure was confirmed by MS.

8. EXAMPLE

MORE CLEAVABLE LINKERS WITH ESTER BONDS

Instrumentation. Melting points were determined on a Kofler block and are uncorrected. $^1$H NMR spectra were recorded on a General Electric QE 300 Instrument. All spectra are reported in ppm relative to tetramethylsilane (δ) using either $CDCl_3$ or $CD_3SOCD_3$ as solvents. UV/VIS absorption spectra were recorded on a Hewlett-Packard HP8452A Diode-Array spectrophotometer using 1-cm quartz cuvette. Amino acid analyses were carried out on a D-500 (Durrum Corp., USA) system. Both analytical and preparative HPLC were carried out on a modular Spectra Physics system using Vydac (0.46×250 mm, 5 μm, flow 1 ml/min) and Vydac (10×250 mm, 10 μm, flow 3 ml/min) C-18 columns, respectively.

General Procedures. Flash chromatography was performed with Merck Silica gel 60 (40–63 μm). Thin-layer chromotography was performed either on Silufol UV 254 (Kavalier, Czechoslovakia) or on Merck DC-Alufolien Kieselgel 60. Preparative thin-layer chromatography was performed on Whatman Silica gel 60A plates (1 mm thickness). The spots were detected by fluorescence quenching or by spraying with a dilute ethanolic ninhydrin solution. Reaction solutions were concentrated using a rotary evaporator (at 2.0–2.6 kPa).

Materials. Unless indicated otherwise, commercial-grade solvents were used without further purification. TentaGel (TG) resin (0.21 mmol/g) was received from Rapp-Polymere (Tübingen). Protected amino acids were obtained from Bachem (Torrance, Calif.) Advanced ChemTech (Louisville, Ky.), or Propeptide (Vert-le-Petit, France).

Ddz-Gly-NH—$(CH_2)_3$—OH (15).

To a solution of Ddz-Gly (released from its cyclohexylammonium salt (15 g, 37.8 mmol) by dissolving it in a mixture of 0.5N $KHSO_4$ and EtOAc until the aqueous layer is acidic to Congo pH=3 and extraction) in DMF (120 ml), DIC (6.49 ml, 41.6 mmol), HOBt (5.11 g, 37.8 mmol) and 1-amino-3-propanol (2.89 ml, 37.8 mmol) were added. After stirring overnight at room temperature the reaction mixture was evaporated to dryness. The residue was dissolved in EtOAc and extracted with 0.5N $KHSO_4$ at 0° C., then with saturated aqueous solution of $NaHCO_3$ and brine, dried over $MgSO_4$ and evaporated. Product was dissolved in EtOAC and precipitated with petroleum ether. Yield: 9.8 g (73%), homogeneous on TLC: $R_f$=0.34 (solvent system 1; DCM-:MeOH:AcOH 90:4:1). $^1$H-NMR (300 MHz, $CDCl_3$, 25° C.) δ: 1.64 (m, 2H, NH—$(CH_2)_3$—OH $C^βH_2$), 1.73 (s, 6H, Ddz $CH_3$), 3.37, 3.61 (m, 2H, NH—$(CH_2)_3$—OH $CαH_2$, NH—$(CH_2)_3$—OH $C^γH_2$), 3.75 (d, 2H, Gly $C^αh_2$), 3.79 (s, 6H, Ddz $OCH_3$), 5.38 (t, 1H, NH—$(CH_2)_3$—OH NH), 6.35–6.50 (m, 3H, Ddz ), 6.61 (t, 1H, Gly NH).

Z-Pro-O—$(CH_2)_3$—NH←Gly←Ddz (16).

To a solution of Z-Pro (1.13 g, 4.5 mmol) in DCM (50 ml) DIC (0.77 ml, 4.94 mmol), DMAP (0.092 g, 0.75 mmol) and Ddz-Gly-NH—$(CH_2)_3$—OH (1.59 g, 4.5 mmol) were added. After stirring overnight the solution was subsequently worked up at the same manner as compound 15. Yield: 2.42 g (92%) ; homogeneous on TLC (solvent system 1).

Boc-Glu (OBzl)-Pro-O—$(CH_2)_3$—NH←Gly←Ddz (17).

Compound 2 (15.1 g,25.8 mmol) was dissolved in DMF (150 ml), anhydrous $Na_2CO_3$ (0.05 g) was added and the compound was hydrogenated over 5% Pd/C catalyst (2.8 g) under normal pressure with vigorous stirring for 6 hours (monitored by TLC). The solution was filtered through a pad of Celite. The filtrate was immediately used for coupling with in situ prepared active ester Boc-Glu(OBzl)OBt [Boc-Glu(OBzl)-OH (8.7 g, 25.8.mmol), HOBt (3.49 g, 25.8 mmol), DIC (4.43 ml, 28.4 mmol) in DMF (40 ml)]. The reaction mixture was stirred overnight and then worked up in the same manner as compound 15. The product was precipitated from solvent mixture of EtOAc-PE (ethyl acetate-petroleum ether) and 16 g (80%) of the title product was obtained. $R_f$=0.81 (solvent system 1).

Boc-Glu-Pro-O—$(CH_2)_3$—NH<Gly←Ddz (18).

Compound 3 (16 g, 20.8 mmol) was dissolved in DMF (210 ml) and hydrogenolyzed over 5% Pd/C catalyst and worked up in the same manner as compound 17. The residue after DMF evaporation was precipitated in mixture of EtOAc-PE. Yield: 13.3 g(94%); $R_f$=0.37. $^1$H-NMR (300 MHz, DMSO-$d_6$, 25° C. ) δ:1.36 (s, 9H, BOC), 1.64 (s, 6H, Ddz $CH_3$), 1.68 (m, 2H, NH—$(CH_2)_3$—O $C^βH_2$), 1.8–2.0 (m, 6H, Glu $C^βH_2$, Pro $C^βH_2$ $C^γH_2$), 2.16 (m, 2H, Glu $C^γH_2$), 3.09, (m, 2H, NH—$(CH_2)_3$—O $CαH_2$), 3.50 (m, 2H, Gly $C^{\alpha}H_2$), 3.65 (m, 2H, Pro $C^{\delta}H_2$), 3.73 (s, 6H, Ddz OCH$_3$), 4.01 (m, 2H, NH—(CH$_2$)$_3$—O $C^{65}$ H$_2$), 4.22 (m, 1H, Glu $C^{\alpha}$H), 4.31 (m, 1H, Pro $C^{\alpha}$H), 6.35–6.49 (m, 3H, Ddz ), 7.09 (d, 1H, Glu NH), 7.38 (t, 1H, Gly NH), 8.05 (t, 1H, NH—(CH$_2$)$_{3-O\ NH}$).

Fmoc-Gly-NH—(CH$_2$)$_3$—OH (19).

To a solution of Fmoc-Gly (59.4 g, 200 mmol) in DMF (900 ml), DIC (31.2 ml, 200 mmol) and HOBt (27.0 g, 200 mmol) were added. After stirring for 30 min, 1-amino-3-propanol (16.1 ml, 210 mmol) was added and reaction mixture was stirred for 4 hrs. The mixture was evaporated to dryness and the residue was dissolved in boiling EtOAc and allowed to crystallize overnight. After recrystallization product was washed with cold EtOAc, PE. Yield: 62 g (91%).

Fmoc-Glu (OBu$^t$)-O—(CH$_2$)$_3$—NH←Gly←Fmoc (20).

To a solution of Fmoc-Glu(OBu$^t$)-OH (10.6 g, 24.9 mmol) in a solvent mixture of DMF:DCM (1:1, 100 ml), DIC (4.28 ml, 27.4 mmol), Fmoc-Gly-NH—(CH$_2$)$_3$—OH (8.5 g, 24.9 mmol) and DMAP (0.31 g, 2.49 mmol) were added. After stirring overnight, solvents were evaporated and the residue was dissolved in EtOAc and extracted with 1M HCl, 10% NaHCO$_3$, brine, dried over MgSO$_4$and evaporated. The product was crystallized from EtOAc-PE (17.5 g, 94%), R$_f$=0.64 (solvent system 1)). $^1$H-NMR (300 MHz, CDCl$_3$, 25° C.) δ: 1.44 (s, 9H, tBu), 1.88 (m, 2H, NH—(CH$_2$)$_{3-O}$ $_c{^{\beta}H_2}$), 1.95–2.10 (m, 2H, Glu C$^{\beta}$H$_2$), 2.33 (m, 2H, Glu C$^{\gamma}$H$_2$), 3.38, (m, 2H, NH—(CH$_2$)$_{3-O\ C\alpha H2}$), 3.84 (d, 2H, Gly C$^{\alpha}$H$_2$), 4.17–4.27 (m, 2H, NH—(CH$_2$)$_3$—O C$^{\gamma}$H$_2$), 4.31 (m, 1H, Glu C$^{\alpha}$H), 4.30–4.40 (m, 3H, Fmoc OCH$_2$CH—), 5.62 (t, 1H, Gly NH), 5.66 (d, 1H, Glu NH), 6.48 (t, 1H, NH—(CH$_2$)$_{3-O\ NH}$), 7.29–7.75 (m, 8H, Fmoc).

Fmoc-Glu-O—(CH$_2$)$_3$—NH←Gly←Fmoc (21).

Compound 6 (2.0 g, 2.67 mmol) was dissolved in TFA-H$_2$O (95:5) and reaction mixture was stirred for 1 hr. After evaporation of the reaction mixture to dryness it was coevaporated with toluene four times. Crude product was crystallized from EtOAc-PE twice to obtain 1.6 g (87%) of pure product. R$_f$=0.38 (solvent system 1). $^1$H-NMR (300 MHz, DMSO-d$_6$, 25° C.) δ: 1.71 (m, 2H, NH—(CH$_2$)$_3$—O C$^{\beta}$H$_2$), 1.81–1.98 (m, 2H, Glu C$^{\beta}$H$_2$), 2.32 (m, 2H, Glu C$^{\gamma}$H$_2$), 3.12, (m, 2H, NH—(CH$_2$)$_3$—O CαH$_2$), 3.58 (d, 2H, Gly C$^{\alpha}$H$_2$), 4.06 (m, 2H, NH—(CH$_2$)$_3$—O C$^{\gamma}$H$_2$), 4.20–4.30 (m, 3H, Fmoc OCH$_2$CH—), 7.76 (d, 1H, Glu NH), 7.47 (t, 1H, Gly NH), 7.32–7.89 (m, 8H, Fmoc), 7.86 (t, 1H, NH—(CH$_2$)$_3$—O NH).

Fmoc-Glu(O—(CH$_2$)$_3$—NH←Gly←Fmoc) -OBu$^t$ (22).

Fmoc-Glu-OBu$^t$ (25.0 g, 58.7 mmol) dissolved in DMF-DCM mixture (1:1, 1200 ml) was coupled with Fmoc-Gly-NH—(CH$_2$)$_3$—OH (22.0 g, 64.6 mmol) in the presence of DIC (10.1 ml, 64.6 mmol) and DMAP (0.71 g, 5.8 mmol) overnight and the reaction mixture was worked up in the same manner as described for compound 20. Crystallization from EtOAc-PE afforded 34.2 g (78%) of the product. R$_f$=0.70 (solvent system 1) $^1$H-NMR (300 MHz, DMSO-d$_6$, 25° C.) δ: 1.38 (s, 9H, tBu), 1.71 (m, 2H, NH—(CH$_2$)$_3$—O C$^{\beta}$H$_2$), 1.80–1.96 (m, 2H, Glu C$^{62}$ H$_2$), 2.37 (m, 2H, Glu C$^{\gamma}$H$_2$), 3.13 (m, 2H, NH—(CH$_2$)$_{3-O}$ $_c{^{\alpha}H_2}$), 3.58 (d, 2H, Gly C$^{\alpha}$H$_2$), 3.93 (m, 1H, Glu C$^{\alpha}$H), 4.01 (m, 2H, NH—(CH$_2$)$_3$—O C$^{\gamma}$H$_2$), 4.20–4.30 (m, 3H, Fmoc OCH$_2$CH—), 7.32–7.89 (m, 8H, Fmoc), 7.47 (t, 1H, Gly NH), 7.67 (d, 1H, Glu NH), 7.85 (t, 1H, NH—(CH$_2$)$_3$—O NH).

Fmoc-Glu(O—(CH$_2$)$_3$—NH←Gly←Fmoc)-OH (23).

The tert butyl protecting group of compound 22 (33.0 g, 44.1 mmol) was cleaved in the same manner as described for compound 21. The same work up afforded a yield 26.3 g (86%). $^1$H-NMR (300 MHz, DMSO-d$_6$, 25° C.) δ: 1.72 (m, 2H, NH—(CH$_2$)$_3$—O C$^{\beta}$H$_2$), 1.83–1.98 (m, 2H, Glu C$^{\beta}$H$_2$), 2.38 (m, 2H, Glu C$^{\gamma}$H$_2$), 3.13 (m, 2H, NH—(CH$_2$)$_3$—O CαH$_2$), 3.58 (d, 2H, Gly C$^{\alpha}$H$_2$), 4.018 (m, 2H, NH—(CH$_2$)$_3$—O C$^{\gamma}$H$_2$), 4.02 (m, 1H, Glu C$^{\alpha}$H), 4.20–4.30 (m, 3H, Fmoc OCH$_2$CH—), 7.32–7.89 (m, 8H, Fmoc), 7.48 (t, 1H, Gly NH), 7.64 (d, 1H, Glu NH), 7.86 (t, 1H, NH—(CH$_2$)$_3$—O NH).

Boc-Glu(Fmoc-Lys-TentaGel)-Pro-O—(CH$_2$)$_3$—NH←Gly←Ddz (linker-resin construct releasable by diketopiperazine formation). TentaGel (0.1 g, substitution 0.23 mequiv NH$_2$/g) was subjected to solid phase synthesis using the following protocol

| step | reagent | time |
| --- | --- | --- |
| 1 | 5% DIEA/DMF | 2 × 5 min |
| 2 | DMF wash | 10 × 2 min |
| 3 | Fmoc-Lys(Boc)/BOP | until Kaiser test is negative |
| 4 | repeat step 2 | |
| 5 | DCM | 10 × 2 min |
| 6 | TFA/DCM/anisole (10/10/1) | 1 × 30 min |
| 7 | repeat step 5 | |
| 8 | 5% DIEA/DCM | repeat until pH = 8 |
| 9 | repeat step 2 | |
| 10 | linker/BOP | until Kaiser test is negative |
| 11 | repeat step 2 | |

Model dipeptide synthesis and control release from the peptide resin construct: Glu(H-Trp-Gly-Lys-TentaGel)-Pro-O—(CH$_2$)$_3$—NH<-Gly<-Gly<-Trp.2HCl. Synthesis of dipeptide used the following protocol:

| step | reagent | time |
| --- | --- | --- |
| 1 | 2% TFA/DCM | 30 min |
| 2 | DCM wash | 10 × 2 min |
| 3 | DMF wash | 10 × 2 min |
| 4 | 50% piperidine/DMF | 10 min |
| 5 | repeat step 3 | |
| 6 | Fmoc-Gly/BOP | until Kaiser test is negative |
| 7 | repeat step 3 | |
| 8 | repeat step 4 | |
| 9 | repeat step 3 | |
| 10 | Fmoc-Trp/BOP | |
| 11 | repeat step 3 | |
| 12 | repeat step 4 | |
| 13 | repeat step 5 | |
| 14 | TFA/DCM/anisole (10/10/1) | 30 min |
| 15 | repeat step 2 | |
| 16 | MeOH | 10 × 2 min |
| 17 | 0.01% HCl | |

Peptide-resin (4 mg) was added to stirred buffer solution pH 8.5 (100 mmol bicarbonate buffer) in a cuvette of a scanning UV spectrometer (Hewlett-Packard, HP1050 (HPUV)). Using an interval of 3 sec, multiple scans of the UV spectrum from 200–500 nm were obtained and the kinetics of release of free Trp-Gly-Gly-NH—(CH$_2$)$_3$—OH was followed (FIG. 5). Maximal release of 0.17 mmol/g (theory 0.19 mmol/g) was achieved.

Fmoc-Glu(Fmoc-nys-TentaGel)-O—(CH$_2$)$_3$—NH←Gly←Fmoc (hydrolytically releasable linker-resin construct). A second arm of the doubly cleavable linker (compound 21) was coupled to Fmoc-Lys-TG using analogous protocol for solid phase synthesis as described above. Model dipeptide (Gly-Trp-Glu(Gly-Trp-Lys-TentaGel)-O—(CH$_2$)$_3$—NH<-Gly<-Trp<-Gly) was synthesized using the same protocol as well. In order to check stability of the second arm of EDC linker, stability of this arm was tested under the conditions of the first release. Peptide-resin (3 mg) was added to stirred buffer solution of pH 8.5 in cuvette of the UV spectrophotometer and by 3 s scans the stability of this ester bond was measured (FIG. 6). No significant release of the peptide was observed. This test proved the stability of the second arm at pH 8.5.

Control release was done in the same manner (following the kinetics by UV spectroscopy) as described for the first release using a 0.3% NaOH solution (FIG. 7). Release 0.18 mmol/g (theory 0.19 mmol/g) was achieved.

Multiple cleavable linker:

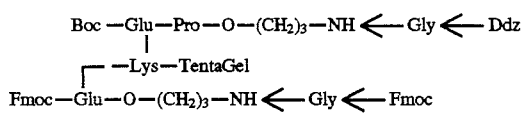

TentaGel (20.0 g, substitution 0.23 mequiv $NH_2$/g) was subjected to solid phase synthesis using the following protocol:

| step | reagent | time |
| --- | --- | --- |
| 1 | 5% DIEA/DMF | 2 × 5 min |
| 2 | DMF wash | 10 × 2 min |
| 3 | Fmoc-Lys(Boc)/BOP | until Kaiser test is negative |
| 4 | repeat step 2 | |
| 5 | DCM | 10 × 2 min |
| 6 | TFA/DCM/anisole (10/10/1) | 1 × 30 min |
| 7 | repeat step 5 | |
| 8 | 5% DIEA/DCM | until pH = 8 |
| 9 | repeat step 2 | |
| 10 | 1st arm/BOP (compound 4) | until Kaiser test is negative |
| 11 | repeat step 2 | |
| 12 | 50% piperidine/DMF | 10 min |
| 13 | repeat step 2 | |
| 14 | 2nd arm/BOP (compound 7) | until Kaiser test is negative |
| 15 | repeat step 2 | |
| 16 | DMAA | 10 × 2 min |

A second multiple cleavable linker format:

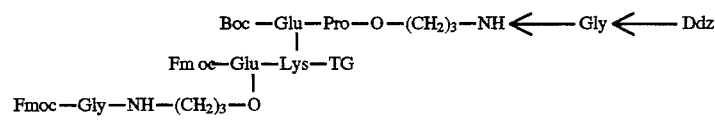

Tentagel (20.0 g, substitution 0.23 mequiv $NH_2$/g) was subjected to solid phase synthesis using the following protocol

| step | reagent | time |
| --- | --- | --- |
| 1 | 5% DIEA/DMF | 2 × 5 min |
| 2 | DMF wash | 10 × 2 min |
| 3 | Fmoc-Lys(Boc)/BOP | until Kaiser test is negative |
| 4 | repeat step 2 | |
| 5 | DCM | 10 × 2 min |
| 6 | TFA/DCM/anisole (10/10/1) | 1 × 30 min |
| 7 | repeat step 5 | |
| 8 | 5% DIEA/DCM | until pH = 8 |
| 9 | repeat step 2 | |
| 10 | 1st arm /BOP (compound 4) | until Kaiser test is negative |
| 11 | repeat step 2 | |
| 12 | 50% piperidine/DMF | 10 min |
| 13 | repeat step 2 | |
| 14 | 2nd arm/BOP (compound 9) | until Kaiser test is negative |
| 15 | repeat step 2 | |
| 16 | DMAA | 10 × 2 min |

H-Glu(OBzl)-O—$(CH_2)_3$—NH←Gly←Fmoc (24).

Boc-Glu(OBzl) (10 mmol, 3.37 g) was dissolved in 50 ml of DMF and activated with DIC (10 mmol, 1.58 ml) in the presence of HOBt (10 mmol, 1.53 g) and 4-dimethylaminopyridine (3 mmol, 0.36 g). Fmoc-Gly-NH—$(CH_2)_3$—OH (10 mmol, 3.54 g) was added and reaction mixture stirred overnight. The DMF was evaporated under reduced pressure, reaction mixture extracted with ether and the oily residue was evaporated. TFA (50 ml) was added, the solution stirred for 60 min, the TFA evaporated, and the oily residue was triturated with ether and evaporated to dryness. Crude product was dissolved in AcOEt, extracted with 3% aqueous HCl (3 times), and the aqueous extracts were washed with AcOEt, neutralized by a saturated solution of $NaHCO_3$. The product was extracted 3 times with AcOEt, extracts dried by anhydrous $MgSO_4$, and the AcOEt evaporated. Yield 5.5 g (93%). Tlc on silicagel plate showed one UV absorbing spot, $R_f$ 0.40 in $CHCl_3$: MeOH: ACOH (90:9:1).

Linker I: Boc-Pro-Glu-O—$(CH_2)_3$—NH←Gly←Fmoc (25).

H-Glu(OBzl)-O—$(CH_2)_3$—NH<-Gly<-Fmoc (9.3 mmol, 5.5 g) was treated overnight with TFA (50 ml) containing 10% of DMS. The TFA was evaporated, and the reaction mixture was triturated with PE (3 times) and ether (3 times) and evaporated to dryness. Boc-Pro (3.3 mmol, 0.71 g) was dissolved in DMF (20 ml), activated with DIC (3.3 mmol, 0.52 ml) in the presence of HOBt (3.3 mmol, 0.49 g) and H-Glu-O—$(CH_2)_3$—NH<-Gly<-Fmoc (3.3 mmol, 1.6 g) was added. The pH was adjusted to 8 with DIEA (wetted paper) and the reaction mixture was stirred overnight. DMF was evaporated under reduced pressure, the oily product was dissolved in AcOEt, and extracted with a solution of $NaHCO_3$ (5 times). The combined extracts were extracted with AcOEt, acidified by 10% aqueous HCl, product extracted to AcOEt (3 times), washed with water (3 times), dried by $MgSO_4$, and AcOEt was evaporated. Yield 1.0 g (16%) of foamy product. Tlc on silicagel plate showed one UV absorbing spot, $R_f$ 0.60 in $CHCl_3$: MeOH: ACOH (90:9:1). $^1$NMR (300 MHz, DMSO, 27° C.) δ: 1.33 (9H, Boc $CH_3$), 1.72 (2H, NH—$(CH_2)_3$—O $C^\beta H_2$), ~1.8 (4H, Pro $C^\beta H_2$ and $C^\gamma H_2$), ~1.9 (2H, Glu $C^\beta H_2$), 2.31 (2H, Glu $C^\gamma H_2$), 3.13 (2H, NH—$(CH_2)_3$—O $C^\alpha H_2$), 3.27 and 3.35 (2H, Pro $C^\delta H_2$), 3.59 (2H, Gly $CH_2$), 4.04 (2H, NH—$(CH_2)_3$—O $C^\gamma H_2$), 4.11 (1H, Pro $C^\alpha H$), 4.27 (1H, Glu $C^\alpha H$), 4.2–4.3 (3H, Fmoc $CH_2$ and CH), 7.47 (1H, Gly NH), 7.33, 7.42, 7.72, and 7.89 (8H, Fmoc aromatic H), 7.86 (1H, NH—(CH$_2$)$_3$—O NH), 8.23 (1H, Glu NH).

H-Pro-O—(CH$_2$)$_3$—NH←Gly←Fmoc (26).

Boc-Pro (10 mmol, 2.15 g) was dissolved in DMF (50 ml), activated with DIC (10 mmol, 1.58 ml) in the presence of HOBt (10 mmol, 1.53 g) and 4-dimethylaminopyridine (3 mmol, 0.36 g). Fmoc-Gly-NH—(CH$_2$)$_{3-OH}$ (10 mmol, 3.54 g) was added and reaction mixture stirred overnight. DMF was evaporated under reduced pressure, the oily residue was dissolved in AcOEt, and precipitate filtered. AcOEt solution was extracted with 3% aqueous HCl (3 times), water, saturated solution of NaHCO$_3$, and water. The solution was dried over MgSO$_4$ and the AcOEt evaporated to dryness (4.2 g). TFA (50 ml) was added, the solution stirred for 60 min, and TFA was evaporated. The oily residue was evaporated with toluene (3 times), product dissolved in AcOEt and precipitated with ether. Yield 1.4 g (31%). Tlc on silicagel plate showed one UV absorbing spot, R$_f$ 0.10 in CHCl$_3$: MeOH: ACOH (90:9:1).

Linker II: Z-Glu-Pro-O—(CH$_2$)$_3$—NH←Gly←Fmoc (27).

Z-Glu(OtBu) (20 mmol, 6.74 g) was dissolved in DMF (50 ml), activated with DIC (20 mmol, 3.12 ml) in the presence of HOBt (20 mmol, 3.06 g), and H-Pro-O—(CH$_2$)$_3$—NH<-Gly-<-Fmoc (26 mmol, 12 g) was added. The pH was adjusted to 8 with DIEA (wetted paper) and the reaction mixture was stirred overnight. DMF was evaporated under reduced pressure, and the oily product was dissolved in AcOEt, extracted with a solution of NaHCO$_3$ (3 times), water, 3% aqueous HCl (3 times), and water. The organic layer was dried by MgSO$_4$, and AcOEt evaporated. The oily residue (8.1 g) was dissolved in DCM (20 ml) and TFA (100 ml) was added. After 60 min the reaction mixture was evaporated, the oily residue evaporated with toluene (3 times) and dissolved in AcOEt. The product was extracted to a saturated solution of NaHCO$_3$ (5 times), and combined extracts were washed with AcOEt, acidified with solution of KHSO$_4$. The product was extracted to AcOEt (3 times), washed with water, dried over MgSO$_4$ and AcOEt was evaporated. Yield 4.3 g (30%) of foamy product. Tlc on silicagel plate showed one UV absorbing spot, R$_f$ 0.50 in CHCl$_3$: MeOH: ACOH (90:9:1). $^1$NMR (300 MHz, DMSO, 27° C.) δ: 1.72 (2H, NH—(CH$_2$)$_{3-O}$ $_c$$^\beta$H$_2$), ~1.8 (6H, Pro C$^\beta$H$_2$ and C$^\gamma$H$_2$, Glu C$^\beta$H$_2$), 2.34 (2H, Glu C$^\gamma$H$_2$), 3.13 (2H, NH—(CH$_2$)$_3$—O C$^\alpha$H$_2$), 3.58 (2H, Gly CH$_2$), ~3.68 (2H, Pro C$^\delta$H$_2$), 4.04 (2H, NH—(CH2)3—OH C$^{96}$ H$_2$), 4.2–4.3 (3H, Fmoc CH$_2$ and CH), ~4.3 (1H, Pro C$^\alpha$H), 5.01 (2H, Z CH$_2$), 7.35 (5H, Z aromatic), 7.33, 7.42, 7.72, and 7.89 (8H, Fmoc aromatic H), 7.84 (1H, NH—(CH$_2$)$_3$—O NH).

Attachment of linkers I and II to TentaGel. TentaGel (1 g, substitution 0.23 in mequiv. NH$_2$/g) was preswollen in DMF (10 ml plastic syringe equipped with polypropylene frit). To a solution of linker (0.5 mmol) in DMF (2 ml), HOBt (0.5 mmol, 75 mg) and DIC (0.5 mmol, 80 μl) were added and the solution was transferred to the syringe containing the TG. After overnight coupling the resin was washed with DMF (5 times) and the Fmoc group was removed by 10 min treatment with 50% piperidine in DMF. Fmoc release was quantified by measuring the absorbance (302 nm) of piperidine solution and combined washes.

Control Release Reactions. Fmoc-Trp in DMF solution was activated by DIC in the presence of HOBt and coupled in 3 molar excess to a linker on TG. After washing with DMF, Fmoc group was removed by 50% piperidine in DMF for 10 min, and the resin was washed with DMF. The absorbance of the piperidine solution with combined washes was read at 302 nm and Fmoc release quantified. The resin was washed with DCM (5 times) and treated with TFA containing different scavengers (see Table 1), washed with DCM, MeOH and dried. A sample (ca 10 mg) was treated overnight with aqueous buffer solution pH 8.5, the absorbance of the solution was read at 280 nm, the resin was washed with water and aqueous NaOH (0.5%) was added. After 4 h the absorbance was read at 280 nm and the amount of Trp containing peptide calculated.

TABLE 3

Releases (in mmol/g) of Trp Containing Peptides from Linkers

| Linker | Fmoc release | TFA treatment | pH 8.5 | pH 13 |
|---|---|---|---|---|
| (I) | 0.195 | Reag K, 2 h | 0.070 | 0.106 |
| (II) | 0.089 | None | 0.004 | 0.080 |
| (II) | 0.089 | Reag K, 2 h | 0.012 | 0.067 |
| (II) | 0.089 | DMS/TFA, 2 h | 0.049 | 0.033 |
| (II) | 0.089 | TA/TFA, 2 h | 0.045 | 0.039 |
| (II) | 0.089 | DMS/TFA, 18 h | 0.072 | |

TFA, trifluoroacetic acid; reagent K, 82.5% TFA, 5% thioanisole, 5% cresol, 5% water, 2.5% ethanedithiol; DMS, dimethylsulfide; TA, thioanisole.

Table 3 shows that a diketopiperazine linker protected with a Boc protecting group is deprotected upon treatment with reagent K, containing 95% TFA. However, since the linker was the more slowly cleaving Pra-Glu combination, only about 28% of the tryptophan label was released. In contrast, the linker protected with the Z (benzyloxycarbonyl) protecting group was not as susceptible to cleavage at pH, even though the more rapidly cleaved Glu-Pro linker was used. However, there was some "leakage", so the Z blocking group, while usable, was not ideal in combination with the Boc protecting group for orthogonal cleavable linkers. Another group, such as Alloc, which is removed by hydrogenolysis, may be a better choice in combination with Boc. Certain Z derivatives may also be useful.

The present invention is not to be limited in scope by the specific embodiments described herein since such embodiments are intended as but single illustrations of one aspect of the invention and any microorganisms which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various references are cited herein, the disclosures of which are incorporated by reference herein in their entirety.

What is claimed is:

1. A solid phase support having the structure:

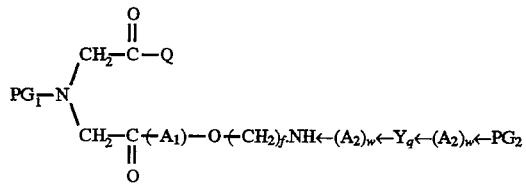

wherein

PG$_1$ is a protecting group selected from the group consisting of Boc, Npys, Alloc, Z and modified Z group;

PG$_2$ is a protecting group selected from the group consisting of Fmoc, Boc, Npys, Alloc, Z and modified Z group;

A$_1$ and each A$_2$ are independently an α-amino acid;

f is 2–6;

each w is independently 0 or a positive integer;

Y is selected from the group consisting of p-hydroxymethylbenzoic acid, hydroxyacetic acid, serine and the 3-hydroxypropylamide of succinic acid;

q is 0 or 1; and

Q is selected from the group consisting of polystyrene resin, poly(dimethylacrylamide)-grafted styrene co-divinylbenzene, polyamide resin, polystyrene resin grafted with polyethylene glycol, polydimethylacrylamide resin, and polysaccharides.

2. The solid phase support of claim 1, wherein $PG_1$ is BOC;

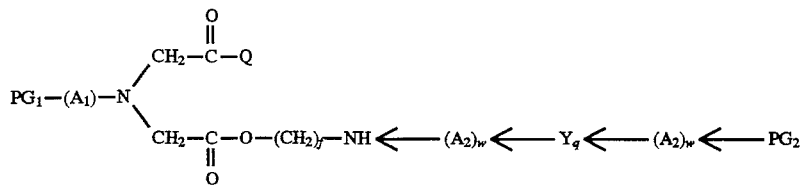

$PG_2$ is Fmoc;

f is 3; and q is 0.

3. The solid phase support of claim 2 wherein $A_1$ is proline.

4. A solid phase support having the structure:

wherein $PG_1$ is a protecting group selected from the group consisting of Boc, Npys, Alloc, Z and modified Z group;

$PG_2$ is a protecting group selected from the group consisting of Fmoc, Boc, Npys, Alloc, Z and modified Z group;

each $A_2$ is independently an α-amino acid;

each f is independently 2–6;

each w is independently 0 or a positive integer;

Y is selected from the group consisting of p-hydroxymethylbenzoic acid, hydroxyacetic acid, serine and the 3-hydroxypropylamide of succinic acid;

each q is independently 0 or 1; and

Q is selected from the group consisting of polystyrene resin, poly(dimethylacrylamide)-grafted styrene co-divinylbenzene, polyamide resin, polystyrene resin grafted with polyethylene glycol, polydimethylacrylamide resin, and polysaccharides.

5. The solid phase support of claim 4, wherein $PG_1$ is BOC;

$PG_2$ is Fmoc;

f is 3; and q is 0.

6. A solid phase support having the structure:

wherein $PG_1$ is a protecting group selected from the group consisting of Boc, Npys, Alloc, Z and modified Z group;

$PG_2$ is a protecting group selected from consisting of Fmoc, Boc, Npys, Alloc, Z and modified Z group;

$A_1$ and each $A_2$ are independently an α-amino acid;

f is 2–6;

each w is independently 0 or a positive integer;

Y is selected from the group consisting of p-hydroxymethylbenzoic acid, hydroxyacetic acid, serine and the 3-hydroxypropylamide of succinic acid;

q is 0 or 1; and

Q is selected from the group consisting of polystyrene resin, poly(dimethylacrylamide)-grafted styrene co-divinylbenzene, polyamide resin, polystyrene resin grafted with polyethylene glycol, polydimethylacrylamide resin, and polysaccharides.

7. The solid phase support of claim 6, wherein $PG_1$ is BOC;

$PG_2$ is Fmoc;

f is 3; and q is 0.

8. The solid phase support of claim 7 wherein $A_1$ is glycine.

9. A solid phase support having the structure:

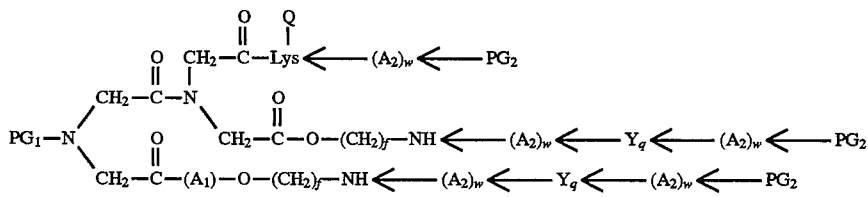

wherein
> PG$_1$ is a protecting group selected from the group consisting of Boc, Npys, Alloc, Z and modified Z group;
>
> each PG$_2$ is independently a protecting group selected from the group consisting of Fmoc, Boc, Npys, Alloc, Z and modified Z group;
>
> A$_1$ and each A$_2$ are independently an α-amino acid;
>
> each f is independently 2–6;
>
> each w is independently 0 or a positive integer;
>
> each Y is independently selected from the group consisting of p-hydroxymethylbenzoic acid, hydroxyacetic acid, serine and the 3-hydroxypropylamide of succinic acid;
>
> each q is independently 0 or 1; and
>
> Q is selected from the group consisting of polystyrene resin, poly(dimethylacrylamide)-grafted styrene co-divinylbenzene, polyamide resin, polystyrene resin grafted with polyethylene glycol, polydimethylacrylamide resin, and polysaccharides.

10. The solid phase support of claim 9, wherein
> PG$_1$ is BOC;
> PG$_2$ is Fmoc;
> f is 3; and
> q is 0.

11. The solid phase support of claim 10 wherein A$_1$ is proline.

12. A solid phase support having the structure:

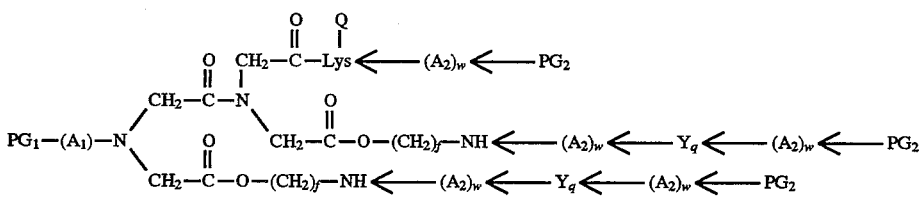

wherein
> PG$_1$ is a protecting group selected from the group consisting of Boc, Npys, Alloc, Z and modified Z group;
>
> each PG$_2$ is independently a protecting group selected from the group consisting of Fmoc, Boc, Npys, Alloc, Z and modified Z group;
>
> A$_1$ and each A$_2$ are independently an α-amino acid;
>
> each f is independently 2–6;
>
> each w is independently 0 or a positive integer;
>
> each Y is independently selected from the group consisting of p-hydroxymethylbenzoic acid, hydroxyacetic acid, serine and the 3-hydroxypropylamide of succinic acid;
>
> each q is independently 0 or 1; and
>
> Q is selected from the group consisting of polystyrene resin, poly(dimethylacrylamide)-grafted styrene co-divinylbenzene, polyamide resin, polystyrene resin grafted with polyethylene glycol, polydimethylacrylamide resin, and polysaccharides.

13. The solid phase support of claim 12, wherein
> PG$_1$ is BOC;
> PG$_2$ is Fmoc;
> f is 3; and
> q is 0.

14. The solid phase support of claim 13 wherein A$_1$ is glycine.

15. The solid phase support of claim 4, wherein
> PG$_1$ is BOC;
> PG$_2$ is Fmoc;
> f is 3;
> q is 0; and
> Y is the 3-hydroxypropylamide of succinic acid.

16. A solid phase support having the structure:

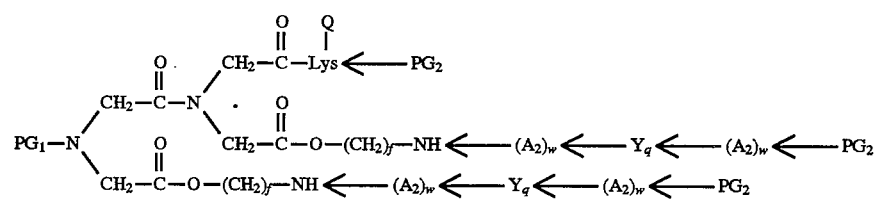

wherein

PG$_1$ is a protecting group selected from the group consisting of Boc, Npys, Alloc, Z and modified Z group;

each PG$_2$ is independently a protecting group selected from the group consisting of Fmoc, Boc, Npys, Alloc, Z and modified Z group;

each A$_2$ is independently an α-amino acid;

each f is independently 2–6;

each w is independently 0 or a positive integer;

each Y is independently selected from the group consisting of p-hydroxymethylbenzoic acid, hydroxyacetic acid, serine and the 3-hydroxypropylamide of succinic acid;

each q is independently 0 or 1; and

Q is selected from the group consisting of polystyrene resin, poly(dimethylacrylamide)-grafted styrene co-divinylbenzene, polyamide resin, polystyrene resin grafted with polyethylene glycol, polydimethylacrylamide resin, and polysaccharides.

17. The solid phase support of claim 16, wherein

PG$_1$ is BOC;

PG$_2$ is Fmoc;

f is 3; and q is 0.

18. A solid phase support having the structure:

wherein $$PG_1-N \begin{matrix} CH_2-C(=O)-N \\ CH_2-C(=O)-Lys \leftarrow PG_2 \end{matrix} \begin{matrix} CH_2-C(=O)-O-(CH_2)_f-NH \leftarrow (A_2)_w \leftarrow Y_q \leftarrow (A_2)_w \leftarrow PG_2 \\ Q\ CH_2-C(=O)-O-(CH_2)_f-NH \leftarrow (A_2)_w \leftarrow Y_q \leftarrow (A_2)_w \leftarrow PG_2 \end{matrix}$$

PG$_1$ is a protecting group selected from the group consisting of Boc, Npys, Alloc, Z and modified Z group;

each PG$_2$ is independently a protecting group selected from the group consisting of Fmoc, Boc, Npys, Alloc, Z and modified Z group;

each A$_2$ is independently an α-amino acid;

each f is independently 2–6;

each w is independently 0 or a positive integer;

each Y is independently selected from the group consisting of p-hydroxymethylbenzoic acid, 2-hydroxy acetic acid, 3-hydroxy, or the 3-hydroxypropylamide of succinic acid;

each q is independently 0 or 1; and

Q is selected from the group consisting of polystyrene resin, poly(dimethylacrylamide)-grafted styrene co-divinylbenzene, polyamide resin, polystyrene resin grafted with polyethylene glycol, polydimethylacrylamide resin, and polysaccharides.

19. The solid phase support of claim 16, wherein

PG$_1$ is BOC;

PG$_2$ is Fmoc;

f is 3; and q is 0.

20. The solid phase support of claim 1 which further comprises a second linker that is acid-labile, base-labile, photolabile, or which second linker can be cleaved by an oxidizing agent, a reducing agent, a nucleophile, or an electrophile.

21. The solid phase support of claim 20, wherein said second linker is selected from the group consisting of ONb, hydroxymethylbenzoic acid, hydroxyacetic acid, and a dipeptide in which the C-terminal amino acid residue is covalently attached via an ester bond to the solid phase support.

22. The solid phase support of claim 21, wherein said second linker is a dipeptide selected from the group consisting of Glu-Pro and Asp-Pro.

23. The solid phase support of claim 1, which further comprises a second linker which is a benzhydrylamine handle of the structure:

[Structure: two phenyl rings connected through a central CH bearing NHD; first phenyl ring bears ZZ and (X$^1$)$_a$ and optionally (Y)$_c$; second phenyl ring bears (X$^2$)$_b$ and optionally (Y)$_d$]

wherein the phenyl group bearing (X$^1$)$_a$, ZZ and optionally (Y)$_c$ is referred to as a first phenyl group, and the phenyl group bearing (X$^2$)$_b$ and optionally (Y)$_d$ is referred to as a second phenyl group;

X$^1$ is selected from the group consisting of —SR$^1$, —S(O)R$^1$, and —S(O)$_2$R$^1$, each X$^1$ being in an ortho or para position, with respect to the carbon atom of the handle bearing NHD, on the first phenyl group;

R$^1$ is a C$_1$–C$_{10}$ hydrocarbon group;

ZZ is —OR$^3$, being in an ortho or para position, with respect to the carbon atom of the handle bearing NHD, on the first phenyl group;

R$^3$ is a C$_1$–C$_{10}$ hydrocarbon group substituted with a carboxyl group for coupling to a solid phase support;

X$^2$ is selected from the group consisting of —SR$^2$, —S(O)R$^2$, and —S(O)$_2$R$^2$, each X$^2$ being in an ortho or para position, with respect to the carbon atom of the handle bearing NHD, on the second phenyl group;

R$^2$ is a C$_1$–C$_{10}$ hydrocarbon group;

Y is —OR$^4$, being in an ortho or para position, with respect to the carbon atom of the handle bearing NHD, not occupied by (X$^1$)$_a$ or ZZ on the first phenyl group and in an ortho or para position, with respect to the carbon atom of the handle bearing NHD, not occupied by (X$^2$)$_b$ on the second phenyl group;

R$^4$ is a C$_1$–C$_{10}$ hydrocarbon group;

a=1–2;

b=1–3;

c=0–1 d=0–1; and

D is selected from the group consisting of —H, a protecting group and an N$^\alpha$-protected aminoacyl moiety, wherein said handle is covalently bonded to said solid phase support via a linkage formed between the ZZ carboxyl group of said handle, and Q.

24. The solid phase support of claim 4 which further comprises a second linker that is acid-labile, base-labile, photolabile, or which second linker can be cleaved by an oxidizing agent, a reducing agent, a nucleophile, or an electrophile.

25. The solid phase support of claim 24, wherein said second linker is selected from the group consisting of ONb, an Asp-Pro dipeptide, hydroxymethylbenzoic acid, hydroxyacetic acid, and a dipeptide in which the C-terminal amino acid residue is covalently attached via an ester bond to the solid phase support.

26. The solid phase support of claim 25, wherein said second linker is a dipeptide selected from the group consisting of Glu-Pro and Asp-Pro.

27. The solid phase support of claim 4, which further comprises a second linker which is a benzhydrylamine handle of the structure:

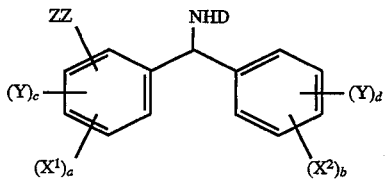

wherein the phenyl group bearing $(X^1)_a$, ZZ and optionally $(Y)_c$ is referred to as a first phenyl group, and the phenyl group bearing $(X^2)_b$ and optionally $(Y)_d$ is referred to as a second phenyl group;

$X^1$ is selected from the group consisting of —$SR^1$, —$S(O)R^1$, and —$S(O)_2R^1$, each $X^1$ being in an ortho or para position, with respect to the carbon atom of the handle bearing NHD, on the first phenyl group;

$R^1$ is a $C_1$–$C_{10}$ hydrocarbon group;

ZZ is —$OR^3$, being in an ortho or para position, with respect to the carbon atom of the handle bearing NHD, on the first phenyl group;

$R^3$ is a $C_1$–$C_{10}$ hydrocarbon group substituted with a carboxyl group for coupling to a solid phase support;

$X^2$ is selected from the group consisting of —$SR^2$, —$S(O)R^2$, and —$S(O)_2R^2$, each $X^2$ being in an ortho or para position, with respect to the carbon atom of the handle bearing NHD, on the second phenyl group;

$R^2$ is a $C_1$–$C_{10}$ hydrocarbon group;

Y is —$OR^4$, being in an ortho or para position, with respect to the carbon atom of the handle bearing NHD, not occupied by $(X^1)_a$ or ZZ on the first phenyl group and in an ortho or para position, with respect to the carbon atom of the handle bearing NHD, not occupied by $(X^2)_b$ on the second phenyl group;

$R^4$ is a $C_1$–$C_{10}$ hydrocarbon group;

a=1–2;

b=1–3;

c=0–1 d=0–1; and

D is selected from the group consisting of —H, a protecting group and an $N^\alpha$-protected aminoacyl moiety, wherein said handle is covalently bonded to said solid phase support via a linkage formed between the ZZ carboxyl group of said handle, and Q.

28. The solid phase support of claim 6 which further comprises a second linker that is acid-labile, base-labile, photolabile, or which second linker can be cleaved by an oxidizing agent, a reducing agent, a nucleophile, or an electrophile.

29. The solid phase support of claim 28, wherein said second linker is selected from the group consisting of ONb, hydroxymethylbenzoic acid, hydroxyacetic acid, and a dipeptide in which the C-terminal amino acid residue is covalently attached via an ester bond to the solid phase support.

30. The solid phase support of claim 29, wherein said second linker is a dipeptide selected from the group consisting of Glu-Pro and Asp-Pro.

31. The solid phase support of claim 6, which further comprises a second linker which is a benzhydrylamine handle of the structure:

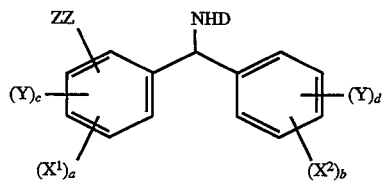

wherein the phenyl group bearing $(X^1)_a$, ZZ and optionally $(Y)_c$ is referred to as a first phenyl group, and the phenyl group bearing $(X^2)_b$ and optionally $(Y)_d$ is referred to as a second phenyl group;

$X^1$ is selected from the group consisting of —$SR^1$, —$S(O)R^1$, and —$S(O)_2R^1$, each $X^1$ being in an ortho or para position, with respect to the carbon atom of the handle bearing NHD, on the first phenyl group;

$R^1$ is a $C_1$–$C_{10}$ hydrocarbon group;

ZZ is —$OR^3$, being in an ortho or para position, with respect to the carbon atom of the handle bearing NHD, on the first phenyl group;

$R^3$ is a $C_1$–$C_{10}$ hydrocarbon group substituted with a carboxyl group for coupling to a solid phase support;

$X^2$ is selected from the group consisting of —$SR^2$, —$S(O)R^2$, and —$S(O)_2R^2$, each $X^2$ being in an ortho or para position, with respect to the carbon atom of the handle bearing NHD, on the second phenyl group;

$R^2$ is a $C_1$–$C_{10}$ hydrocarbon group;

Y is —$OR^4$, being in an ortho or para position, with respect to the carbon atom of the handle bearing NHD, not occupied by $(X^1)_a$ or ZZ on the first phenyl group and in an ortho or para position, with respect to the carbon atom of the handle bearing NHD, not occupied by $(X^2)_b$ on the second phenyl group;

$R^4$ is a $C_1$–$C_{10}$ hydrocarbon group;

a=1–2;

b=1–3;

c=0–1 d=0–1; and

D is selected from the group consisting of —H, a protecting group and an $N^\alpha$-protected aminoacyl moiety, wherein said handle is covalently bonded to said solid phase support via a linkage formed between the ZZ carboxyl group of said handle, and Q.

32. The solid phase support of claim 9 which further comprises a second linker that is acid-labile, base-labile, photolabile, or which second linker can be cleaved by an oxidizing agent, a reducing agent, a nucleophile, or an electrophile.

33. The solid phase support of claim 32, wherein said second linker is selected from the group consisting of ONb, hydroxymethylbenzoic acid, hydroxyacetic acid, and a dipeptide in which the C-terminal amino acid residue is covalently attached via an ester bond to the solid phase support.

34. The solid phase support of claim 33, wherein said second linker is a dipeptide selected from the group consisting of Glu-Pro and Asp-Pro.

35. The solid phase support of claim 9, which further comprises a second linker which is a benzhydrylamine handle of the structure:

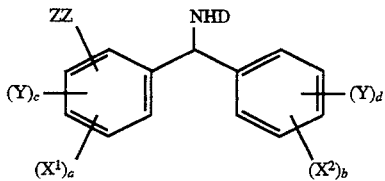

wherein the phenyl group bearing $(X^1)_a$, ZZ and optionally $(Y)_c$ is referred to as a first phenyl group, and the phenyl group bearing $(X^2)_b$ and optionally $(Y)_d$ is referred to as a second phenyl group;

$X^1$ is selected from the group consisting of —$SR^1$, —$S(O)R^1$, and —$S(O)_2R^1$, each $X^1$ being in an ortho or para position, with respect to the carbon atom of the handle bearing NHD, on the first phenyl group;

$R^1$ is a $C_1$–$C_{10}$ hydrocarbon group;

ZZ is —$OR^3$, being in an ortho or para position, with respect to the carbon atom of the handle bearing NHD, on the first phenyl group;

$R^3$ is a $C_1$–$C_{10}$ hydrocarbon group substituted with a carboxyl group for coupling to a solid phase support;

$X^2$ is selected from the group consisting of —$SR^2$, —$S(O)R^2$, and —$S(O)_2R^2$, each $X^2$ being in an ortho or para position, with respect to the carbon atom of the handle bearing NHD, on the second phenyl group;

$R^2$ is a $C_1$–$C_{10}$ hydrocarbon group;

Y is —$OR^4$, being in an ortho or para position, with respect to the carbon atom of the handle bearing NHD, not occupied by $(X^1)_a$ or ZZ on the first phenyl group and in an ortho or para position, with respect to the carbon atom of the handle bearing NHD, not occupied by $(X^2)_b$ on the second phenyl group;

$R^4$ is a $C_1$–$C_{10}$ hydrocarbon group;

a=1–2;
b=1–3;
c=0–1
d=0–1; and

D is selected from the group consisting of —H, a protecting group and an $N^\alpha$-protected aminoacyl moiety, wherein said handle is covalently bonded to said solid phase support via a linkage formed between the ZZ carboxyl group of said handle, and Q.

36. The solid phase support of claim 12 which further comprises a second linker that is acid-labile, base-labile, photolabile, or which second linker can be cleaved by an oxidizing agent, a reducing agent, a nucleophile, or an electrophile.

37. The solid phase support of claim 36, wherein said second linker is selected from the group consisting of ONb, hydroxymethylbenzoic acid, hydroxyacetic acid, and a dipeptide in which the C-terminal amino acid residue is covalently attached via an ester bond to the solid phase support.

38. The solid phase support of claim 37, wherein said second linker is a dipeptide selected from the group consisting of Glu-Pro and Asp-Pro.

39. The solid phase support of claim 12, which further comprises a second linker which is a benzhydrylamine handle of the structure:

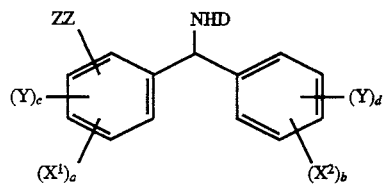

wherein the phenyl group bearing $(X^1)_a$, ZZ and optionally $(Y)_c$ is referred to as a first phenyl group, and the phenyl group bearing $(X^2)_b$ and optionally $(Y)_d$ is referred to as a second phenyl group;

$X^1$ is selected from the group consisting of —$SR^1$, —$S(O)R^1$, and —$S(O)_2R^1$, each $X^1$ being in an ortho or para position, with respect to the carbon atom of the handle bearing NHD, on the first phenyl group;

$R^1$ is a $C_1$–$C_{10}$ hydrocarbon group;

ZZ is —$OR^3$, being in an ortho or para position, with respect to the carbon atom of the handle bearing NHD, on the first phenyl group;

$R^3$ is a $C_1$–$C_{10}$ hydrocarbon group substituted with a carboxyl group for coupling to a solid phase support;

$X^2$ is selected from the group consisting of —$SR^2$, —$S(O)R^2$, and —$S(O)_2R^2$, each $X^2$ being in an ortho or para position, with respect to the carbon atom of the handle bearing NHD, on the second phenyl group;

$R^2$ is a $C_1$–$C_{10}$ hydrocarbon group;

Y is —$OR^4$, being in an ortho or para position, with respect to the carbon atom of the handle bearing NHD, not occupied by $(X^1)_a$ or ZZ on the first phenyl group and in an ortho or para position, with respect to the carbon atom of the handle bearing NHD, not occupied by $(X^2)_b$ on the second phenyl group;

$R^4$ is a $C_1$–$C_{10}$ hydrocarbon group;

a=1–2;
b=1–3;
c=0–1
d=0–1; and

D is selected from the group consisting of —H, a protecting group and an $N^\alpha$-protected aminoacyl moiety, wherein said handle is covalently bonded to said solid phase support via a linkage formed between the ZZ carboxyl group of said handle, and Q.

40. The solid phase support of claim 16 which further comprises a second linker that is acid-labile, base-labile, photolabile, or which second linker can be cleaved by an oxidizing agent, a reducing agent, a nucleophile, or an electrophile.

41. The solid phase support of claim 40, wherein said second linker is selected from the group consisting of ONb, hydroxymethylbenzoic acid, hydroxyacetic acid, and a dipeptide in which the C-terminal amino acid residue is covalently attached via an ester bond to the solid phase support.

42. The solid phase support of claim 41, wherein said second linker is a dipeptide selected from the group consisting of Glu-Pro and Asp-Pro.

43. The solid phase support of claim 16, which further comprises a second linker which is a benzhydrylamine handle of the structure:

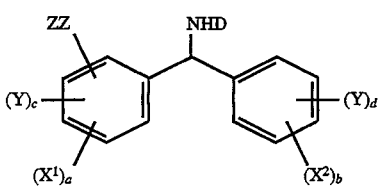

wherein the phenyl group bearing $(X^1)_a$, ZZ and optionally $(Y)_c$ is referred to as a first phenyl group, and the phenyl group bearing $(X^2)_b$ and optionally $(Y)_d$ is referred to as a second phenyl group;

$X^1$ is selected from the group consisting of $—SR^1$, $—S(O)R^1$, and $—S(O)_2R^1$, each $X^1$ being in an ortho or para position, with respect to the carbon atom of the handle bearing NHD, on the first phenyl group;

$R^1$ is a $C_1$-$C_{10}$ hydrocarbon group;

ZZ is $—OR^3$, being in an ortho or para position, with respect to the carbon atom of the handle bearing NHD, on the first phenyl group;

$R^z$ is a $C_1$-$C_{10}$ hydrocarbon group substituted with a carboxyl group for coupling to a solid phase support;

$X^2$ is selected from the group consisting of $—SR^2$, $—S(O)R^2$, and $—S(O)_2R^2$, each $X^2$ being in an ortho or para position, with respect to the carbon atom of the handle bearing NHD, on the second phenyl group;

$R^2$ is a $C_1$-$C_{10}$ hydrocarbon group;

Y is $—OR^4$, being in an ortho or para position, with respect to the carbon atom of the handle bearing NHD, not occupied by $(X^1)_a$ or ZZ on the first phenyl group and in an ortho or para position, with respect to the carbon atom of the handle bearing NHD, not occupied by $(X^2)_b$ on the second phenyl group;

$R^4$ is a $C_1$-$C_{10}$ hydrocarbon group;

a=1–2;

b=1–3;

c=0–1 d=0–1; and

D is selected from the group consisting of —H, a protecting group and an $N^\alpha$-protected aminoacyl moiety, wherein said handle is covalently bonded to said solid phase support via a linkage formed between the ZZ carboxyl group of said handle, and Q.

44. The solid phase support of claim 18 which further comprises a second linker that is acid-labile, base-labile, photolabile, or which second linker can be cleaved by an oxidizing agent, a reducing agent, a nucleophile, or an electrophile.

45. The solid phase support of claim 44, wherein said second linker is selected from the group consisting of ONb, hydroxymethylbenzoic acid, hydroxyacetic acid, and a dipeptide in which the C-terminal amino acid residue is covalently attached via an ester bond to the solid phase support.

46. The solid phase support of claim 45, wherein said second linker is a dipeptide selected from the group consisting of Glu-Pro and Asp-Pro.

47. The solid phase support of claim 18, which further comprises a second linker which is a benzhydrylamine handle of the structure:

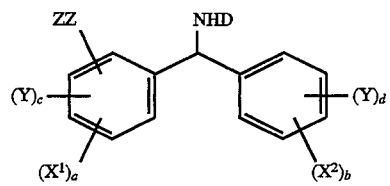

wherein the phenyl group bearing $(X^1)_a$, ZZ and optionally $(Y)_c$ is referred to as a first phenyl group, and the phenyl group bearing $(X^2)_b$ and optionally $(Y)_d$ is referred to as a second phenyl group;

$X^1$ is selected from the group consisting of $—SR^1$, $—S(O)R^1$, and $—S(O)_2R^1$, each $X^1$ being in an ortho or para position, with respect to the carbon atom of the handle bearing NHD, on the first phenyl group;

$R^1$ is a $C_1$-$C_{10}$ hydrocarbon group;

ZZ is $—OR^3$, being in an ortho or para position, with respect to the carbon atom of the handle bearing NHD, on the first phenyl group;

$R^3$ is a $C_1$-$C_{10}$ hydrocarbon group substituted with a carboxyl group for coupling to a solid phase support;

$X^2$ is selected from the group consisting of $—SR^2$, $—S(O)R^2$, and $—S(O)_2R^2$, each $X^2$ being in an ortho or para position, with respect to the carbon atom of the handle bearing NHD, on the second phenyl group;

$R^2$ is a $C_1$-$C_{10}$ hydrocarbon group;

Y is $—OR^4$, being in an ortho or para position, with respect to the carbon atom of the handle bearing NHD, not occupied by $(X^1)_a$ or ZZ on the first phenyl group and in an ortho or para position, with respect to the carbon atom of the handle bearing KTHD, not occupied by $(X^2)_b$ on the second phenyl group;

$R^4$ is a $C_1$-$C_{10}$ hydrocarbon group;

a=1–2;

b=1–3;

c=0–1 d=0–1; and

D is selected from the group consisting of —H, a protecting group and an $N^\alpha$-protected aminoacyl moiety, wherein said handle is covalently bonded to said solid phase support via a linkage formed between the ZZ carboxyl group of said handle, and Q.

* * * * *

UNITED STATES PATENT AND TRADEMARK OFFICE
CERTIFICATE OF CORRECTION

PATENT NO. : 5,635,598

DATED : June 3, 1997

INVENTOR(s) : Michal Lebl, et al.

It is certified that error appears in the above-identified patent and that said Letters Patent is hereby corrected as shown below:

At column 1, line 1, the title reads "Cleavabe Linners" and should read --Cleavable Linkers--.
At column 3, line 10, the patent reads "for multiply" and should read --for multiple--.
At column 3, line 21, and again at column 5, line 51, the patent reads "ester bond linkages" and should read --ester bond linkage--.
At column 8, line 28, the patent reads "Pra-Glu" and should read --Pro-Gly--.
At column 17, line 19, the patent reads "na-growth" and should read --no-growth--.
At column 31, line 2, the patent reads "$(CH_2)_3$-O $C^{65}H_2$" and should read -- $(CH_2)_3$-OH $C^{\alpha}H_2$"
At column 31, line 57, the patent reads "$C^{62}H_2$" and should read -- $C^{\beta}H_2$ --.
At column 32, line 61, the patent reads "-nys-" and should read -- -lys- --.
At column 33, line 49, the patent reads "fm oc" and should read --fmoc--.
At column 35, line 45, the patent reads "$C^{96}H_2$" and should read --$C^{\tau}H_2$--.
At column 36, line 26, the patent reads "Pra" and should read --Pro--.
At column 37, claim 2, there should be no structure. The structure that appears is part of column 38 and belongs to claim 6.
At column 37, claims 3 and 4, an overlap in the printing process renders claim 3 and the structure of claim 4 illegible. They should read as follows:
--3. The solid phase support of claim 2 wherein A1 is proline.--

UNITED STATES PATENT AND TRADEMARK OFFICE
CERTIFICATE OF CORRECTION

PATENT NO. : 5,635,598                                    Page 2 of 2

DATED      : June 3, 1997

INVENTOR(s) : Michal Lebl, et al.

It is certified that error appears in the above-identified patent and that said Letters Patent is hereby corrected as shown below:

--4. A solid phase support having the structure

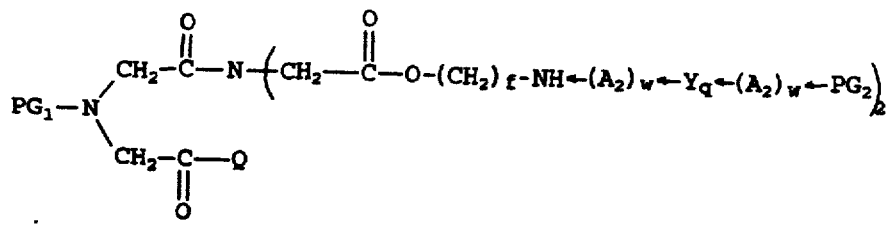

wherein --.

At column 40, it is not clear and should be noted that the final structure on the page is part of claim 16.

Signed and Sealed this

Eighth Day of September, 1998

Attest:

BRUCE LEHMAN

Attesting Officer          Commissioner of Patents and Trademarks